(12) United States Patent
Peeters et al.

(10) Patent No.: US 12,089,304 B2
(45) Date of Patent: Sep. 10, 2024

(54) MELANOPIC LIGHT SYSTEM USING CYAN PUMPED WHITE LEDS

(71) Applicant: SIGNIFY HOLDING B.V., Eindhoven (NL)

(72) Inventors: Martinus Petrus Joseph Peeters, Weert (NL); Rene Theodorus Wegh, Veldhoven (NL)

(73) Assignee: SIGNIFY HOLDING, B.V., Eindhoven (NL)

( * ) Notice: Subject to any disclaimer, the term of this patent is extended or adjusted under 35 U.S.C. 154(b) by 192 days.

(21) Appl. No.: 17/917,212

(22) PCT Filed: Apr. 8, 2021

(86) PCT No.: PCT/EP2021/059151
§ 371 (c)(1),
(2) Date: Oct. 5, 2022

(87) PCT Pub. No.: WO2021/204934
PCT Pub. Date: Oct. 14, 2021

(65) Prior Publication Data
US 2023/0156883 A1    May 18, 2023

(30) Foreign Application Priority Data
Apr. 9, 2020  (EP) .................................... 20169108

(51) Int. Cl.
*H05B 45/20* (2020.01)
*F21K 9/64* (2016.01)
*F21Y 115/10* (2016.01)

(52) U.S. Cl.
CPC .............. *H05B 45/20* (2020.01); *F21K 9/64* (2016.08); *F21Y 2115/10* (2016.08)

(58) Field of Classification Search
None
See application file for complete search history.

(56) References Cited

U.S. PATENT DOCUMENTS

| | | | | |
|---|---|---|---|---|
| 4,600,913 | A | * | 7/1986 | Caine ..................... B60Q 1/302 340/479 |
| 5,150,098 | A | * | 9/1992 | Rakow ................... B60Q 1/444 340/464 |

(Continued)

FOREIGN PATENT DOCUMENTS

| | | |
|---|---|---|
| JP | 2018511386 A | 4/2018 |
| WO | WO-2021204934 A1 * | 10/2021 ............ A61M 21/00 |

*Primary Examiner* — Srinivas Sathiraju

(57) ABSTRACT

A light generating system generating system light, comprising a first and second light generating devices, wherein: the first light generating device generates first device light, the first light generating device comprises (i) a first light source generating first light source light having a first dominant wavelength selected from the range of 470-500 nm, and (ii) a first luminescent material converting part of the first light source light into first luminescent material light; wherein the first device light comprises the first light source light and the first luminescent material light; the first device light has a first color point; the second light generating device generates second device light, the second light generating device comprises (i) a second light source generating second light source light having a second dominant wavelength, and (ii) a second luminescent material configured to convert at least part of the second light source light into second luminescent material light; wherein the second device light comprises the second luminescent material light; and wherein the second device light is white light having a second color point and a second correlated color temperature.

15 Claims, 7 Drawing Sheets

(56) References Cited

U.S. PATENT DOCUMENTS

| | | | | |
|---|---|---|---|---|
| 9,191,574 | B2* | 11/2015 | McMahon | H04N 21/422 |
| 9,264,672 | B2* | 2/2016 | Lynam | H04N 23/55 |
| 9,404,636 | B1* | 8/2016 | Engberg | F21S 8/08 |
| 9,446,713 | B2* | 9/2016 | Lu | B60R 1/002 |
| 9,495,876 | B2* | 11/2016 | Lu | B60W 30/09 |
| 9,829,883 | B1* | 11/2017 | Lavoie | G05D 1/0223 |
| 9,855,890 | B2* | 1/2018 | James | B60K 35/10 |
| 10,174,870 | B2* | 1/2019 | Berardi | F16L 11/12 |
| 10,328,847 | B2* | 6/2019 | Yang | B60Q 1/543 |
| 10,793,067 | B2* | 10/2020 | Ihlenburg | B60R 1/28 |
| 2021/0381678 | A1* | 12/2021 | Spiro | F21V 31/005 |
| 2022/0290842 | A1* | 9/2022 | Vdovin | F21V 9/30 |
| 2023/0189411 | A1* | 6/2023 | Peeters | H05B 45/20 |
| | | | | 315/185 R |

* cited by examiner

MELANOPIC LIGHT SYSTEM USING CYAN PUMPED WHITE LEDS

CROSS-REFERENCE TO PRIOR APPLICATIONS

This application is the U.S. National Phase application under 35 U.S.C. § 371 of International Application No. PCT/EP2021/059151, filed on Apr. 8, 2021, which claims the benefit of European Patent Application No. 20169108.6, filed on Apr. 9, 2020. These applications are hereby incorporated by reference herein.

FIELD OF THE INVENTION

The invention relates to a light generating system as well as to a lamp or luminaire comprising such light generating system.

BACKGROUND OF THE INVENTION

Solid state light emitting devices including adjustable melatonin suppressing effects are known in the art. U.S. Pat. No. 9,039,746, for instance, describes a solid state light emitting device include multiple LED components providing adjustable melatonin suppression effects. Multiple LED components may be operated simultaneously according to different operating modes according to which their combined output provides the same or similar chromaticity, but provides melatonin suppressing effects that differ by at least a predetermined threshold amount between the different operating modes. Switching between operating modes may be triggered by user input elements, timers/clocks, or sensors (e.g., photo sensors). Chromaticity of combined output of multiple LED components may also be adjusted, together with providing adjustable melatonin suppression effects at each selected combined output chromaticity.

SUMMARY OF THE INVENTION

Critical to our sleep/wake cycle is melatonin, a hormone that promotes sleep during night time. Melatonin is a sleep supportive hormone that we only produce around (and during) our usual bedtime. Light exposure during the evening and at night suppresses the natural production of melatonin. When the spectrum of the light is shifted towards lower CCT and intensity levels (like during dawn and dusk), this reduces melatonin suppression and makes the light less disruptive for sleep. During day time, natural daylight with high correlated color temperature (CCT, herein also indicated as "color temperature") and intensity energizes people making them awake and alert. Current high performance LED based lighting apparatus with tunable CCT are able to mimic different phases of daylight, i.e., changes in spectral power distribution and variations in CCT, to a certain extent.

Next to the commonly known cones and rods, the human eye has melanopsin containing photoreceptors, affecting circadian entrainment and melatonin secretion, which are sensitive in a specific wavelength range. The relative spectral sensitivity for the classic receptors (rods and cones) and for the melanopic receptors are provided in FIG. 6 (see also R. J. Lucas, et al., Measuring and using light in the melanopsin age, Trends in Neurosciences, Vol. 37, No. 1, January 2014, pp. 1-9; http://www.sciencedirect.com/science/article/pii/S0166223613001975, the report "CIE TN 003:2015: Report on the First International Workshop on Circadian and Neurophysiological Photometry, 2013" at http://cie.co.at/index.php?i_ca_id=978 (with a link to an excel toolbox http://files.cie.co.at/784_TN003_Toolbox.xls). If the spectral power in the melanopic wavelength range is absent or low, the light exposure will be less suppressive for the melatonin hormone production thus enabling faster sleep onset and more consolidated sleep. If the spectral power in the melanopic range is increased, a light exposure will result in stronger melatonin suppression. In general a light exposure can be said to be more biologically active and more alerting when the power in the melanopic range (and the ability to suppress melatonin at night) is increased. The effectiveness of a given light spectrum in suppressing melatonin production can be expressed in terms of the melanopsin effectiveness factor (MEF). This factor is calculated by multiplying the spectral power distribution of the light emitted by a lighting system (SPD($\lambda$)) with the melanopic sensitivity function (m($\lambda$)) divided by the product of SPD($\lambda$) and the photopic luminosity function (V($\lambda$)), normalized by the areas under the curves of m($\lambda$) and V($\lambda$), see equation 1 (and see also FIG. 1).

$$MEF = \left(\frac{\int_\lambda V(\lambda)d\lambda}{\int_\lambda m(\lambda)d\lambda}\right) \cdot \left(\frac{\int_\lambda SPD(\lambda)m(\lambda)d\lambda}{\int_\lambda SPD(\lambda)V(\lambda)d\lambda}\right) \quad \text{(eq. 1)}$$

This can be simplified to $$MEF = 1.22 \left(\frac{\int_\lambda SPD(\lambda)m(\lambda)d\lambda}{\int_\lambda SPD(\lambda)V(\lambda)d\lambda}\right) \quad \text{(eq. 2)}$$

as $$MEF = 1.22 \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3)}$$

Hence, the above indicated summations are over the visible range of 380-780 nm. By definition, the MEF for an equi-energy light source $MEF_{EE}$ equals 1. Especially, an equi-energy light source has SPD($\lambda$)=constant (for example 1) for all (visible) wavelengths.

The maximum sensitivity of this sensor in the human eye (intrinsically Photosensitive Retinal Ganglion Cells or iPRGCs) is around 490 nm. Stimulation of the iPRGCs during daytime (or the absence of stimulation in the evening) is important to control the circadian rhythm (entrainment to the 24 hours cycle).

The melanopic efficiency of a light spectrum can be calculated using the MDEF (Melanopic D65 Efficiency Factor) (sometimes also indicated as MDER, i.e. Melanopic Daylight Efficacy Ratio). In such instance, instead of an equal energy light source, a D65 source, i.e. CIE Standard Illuminant D65, which is a commonly used standard illuminant defined by the International Commission on Illumination (CIE). MDEF can be defined as the illuminance in lux of a D65 source needed to generate the same stimulation of the iPRGCs per lux of the test source (or test system). The MDEF value of a D65 source is approximately 0.906* the MEF value. Instead of the MDEF value, also the MELR value may be applied. The term MELR refers to melanopic efficacy of luminous radiation (in mW/Lm).

Instead of the MDEF value, also a MELR value (Melanopic efficacy of luminous radiation) may be used. With respect to the calculation of the MDEF value and the MELR value the following can be mentioned. For the test spectrum that is to be evaluated one may calculate how many mW are in the region of the spectrum of the test spectrum (by weighing the spectrum with m(lambda). One can also calculate how many Lm are generated. The ratio of power in mW and lumen in Lm is called MELR value. For a D65 reference spectrum this calculation can also be done. The MELR of D65=1.326 mW/Lm. The ratio of the MELR value of the test spectrum to be evaluated and the MELR value of the reference spectrum (D65) is called MDEF (or MDEF value). MDEF is a value without units.

MELR can thus be expressed in mW/Lm in which the mW is calculated by $\sum_{\lambda=380}^{780} SPD(\lambda)m(\lambda)\Delta\lambda$. The lumens in Lm are calculated in the normal way.

As indicated above, especially the MDEF, which is herein further indicated as MDER, is applied. The MDER is defined as:

$$MDER = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3a)}$$

wherein SPD($\lambda$) is the spectral power distribution of the light emitted by a light generating device, m($\lambda$) is the melanopic sensitivity function, the V($\lambda$) is the photopic luminosity function.

As indicated above, the biological effect of lighting is the product of Illumination (Lux at the eye)*MDER*(Exposure time). Next to that also the time of exposure (morning/evening) determines the effect on people. In normal indoor lighting conditions, the stimulation of the IPRGCs during daytime is too low (e.g. 500 lux in offices, 4000K, MDER~0.6).

It appears desirable to enrich lighting with cyan light. However, using direct cyan emitters in combination with white LEDs to boost the MDER of a spectrum may have one large drawback. The strongly deviating color point (the direct cyan emitter is not a white LED, but blueish/green), prohibits the application in lighting systems without enough (color) mixing. The approach using direct cyan emitters can therefore not be used in e.g. panels (side-lit or direct-lit), or in lighting systems using lenses. These problems may be reduced or even absent in the case that the light emitted by the cyan enhanced LED would be white. However, a tunable system using white LEDs in combination with a cyan pumped LED may enable only a very limited tuning range. In addition, it appears that a cyan pumped white LED with a deep-red phosphor with an emission peak intensity between 640 and 680 nm is very inefficient.

Hence, it is an aspect of the invention to provide an alternative lighting system, which preferably further at least partly obviates one or more of above-described drawbacks. The present invention may have as object to overcome or ameliorate at least one of the disadvantages of the prior art, or to provide a useful alternative.

Hence, in a first aspect the invention provides a light generating system configured to generate system light. The light generating system comprises a first light generating device and a second light generating device. The first light generating device is configured to generate first device light. Especially, the first light generating device comprises (i) a first light source configured to generate first light source light having a first dominant wavelength $\lambda d1$. In specific embodiments, the first dominant wavelength $\lambda d1$ is selected from the range of 470-500 nm. Further, especially the first light generating device comprises (ii) a first luminescent material configured to convert part of the first light source light into first luminescent material light. Especially, the first device light comprises the first light source light and the first luminescent material light. In specific embodiments, the first device light has a first color point. Yet further, the second light generating device is configured to generate second device light. Especially, the second light generating device comprises (i) a second light source configured to generate second light source light having a second dominant wavelength $\lambda d2$. Further, especially the second light generating device comprises (ii) a second luminescent material configured to convert at least part of the second light source light into second luminescent material light. Especially, the second device light comprises the second luminescent material light and optionally the second light source light. In specific embodiments, the second device light has a second color point. Especially, the second device light is white light having a second correlated color temperature Tc2. Especially, in embodiments $\lambda d1-\lambda d2\geq 10$ nm. Yet further, especially the spectral power distributions of the first light source light and the second light source light differ. In specific embodiments, the first color point and the second color point differ at maximum 0.03 for u' and/or at maximum 0.03 for v'. Especially, the color points u' and v' are based on the 10° color matching functions according to CIE S 014-1/E:2006 (see table 2 of CIE S 014-1/E:2006) (herein also indicated as "10° CMFs" and similar phrases). Therefore, especially the invention provides in embodiments a light generating system configured to generate system light, wherein the light generating system comprises a first light generating device and a second light generating device, wherein: (a) the first light generating device is configured to generate first device light, wherein the first light generating device comprises (i) a first light source configured to generate first light source light having a first dominant wavelength $\lambda d1$ selected from the range of 470-500 nm, and (ii) a first luminescent material configured to convert part of the first light source light into first luminescent material light; wherein the first device light comprises the first light source light and the first luminescent material light; and wherein the first device light has a first color point; (b) the second light generating device is configured to generate second device light, wherein the second light generating device comprises (i) a second light source configured to generate second light source light having a second dominant wavelength $\lambda d2$, and (ii) a second luminescent material configured to convert at least part of the second light source light into second luminescent material light; wherein the second device light comprises the second luminescent material light and optionally the second light source light; and wherein the second device light has a second color point (and wherein especially the second device light is white light having a second correlated color temperature Tc2); (c) $\lambda d1-\lambda d2\geq 10$ nm; (d) spectral power distributions of the first light source light and the second light source light differ; and (e) the first color point and the second color point differ at maximum 0.03 for u' and/or at maximum 0.03 for v' (using the 10° color matching functions according to CIE S 014-1/E:2006 (see table 2)).

Herein, color points are especially defined using the 10 degree color matching functions according to CIE S 014-1/E:2006 (see table 2). Color temperatures are based on the CIE 1960 diagram (u,v values, i.e. using the CIE 1931 2 degree color matching functions).

It appears that combining cyan pumped LEDs and blue pumped LEDs with the same color as the second channel allows to generate tunable systems with a large tuning range. In this way, a lighting system may be provided with a fixed or variable MDER, and also having a potentially variable correlated color temperature (CCT). Further, combining cyan pumped LEDs and blue pumped LEDs with the same color may also be used as such for providing a lighting system with an improved MDER as such. In this way, a lighting system may be provided with a fixed or variable MDER, with an essentially fixed correlated color temperature (CCT).

As indicated above, the invention provides a light generating system configured to generate system light, wherein the light generating system comprises a first light generating device and a second light generating device.

The term "first light generating device" may also refer to a plurality of essentially the same light generating devices (such as from the same bin). The term "second light generating device" may also refer to a plurality of essentially the same light generating devices (such as from the same bin). The terms "first light generating device" and "second light generating device" especially refers to devices that are different, especially in one or more spectral properties. Herein, the spectral distributions are different, and e.g. the color rendering indices (CRI) may differ substantially, such as at least 10 points. Hence, the spectral power distributions of the first light source light and the second light source light differ. However, the color points may essentially be the same. Hence, in embodiments the first color point and the second color point may differ at maximum 0.03 for u' and/or at maximum 0.03 for v', such as at maximum 0.02 for u' and/or at maximum 0.02 for v'. Even more especially, in embodiments the first color point and the second color point may differ at maximum 0.01 for u' and/or at maximum 0.01 for v'. For the u' and v' values, especially the 10° color matching functions according to CIE S 014-1/E:2006 (see table 2), are applied, i.e. the 10° color matching functions. Further, the phrase "the light generating system comprises a first light generating device and a second light generating device" does not exclude the presence of other light generating devices. As will be indicated below, in a number of embodiments, yet a further (a third) light generating device may be comprised by the light generating system. Instead of the term "light generating system" also the terms "lighting system" or "system" may herein be applied. Further, instead of the term "light generating device" also the terms "lighting device" or "device" may herein be applied.

Herein, the light generating devices especially comprise solid state light sources (see further also below).

As indicated above, the first light generating device and the second are substantially different, such as providing device light with different spectral power distributions. However, the color point may essentially be the same. Here below, some embodiments are described in relation to the first light generating device and second light generating device.

The first light generating device is configured to generate first device light.

Especially, the first light generating device comprises a first light source configured to generate first light source light having a first dominant wavelength $\lambda d1$. The first light source especially comprises a solid state light source, such as an LED. The first dominant wavelength $\lambda d1$ is especially selected from the range of 470-500 nm. Hence, the first light source is especially a cyan light source, such as a cyan LED. More especially, the first dominant wavelength $\lambda d1$ may be selected from the range of 470-490 nm. Best results were obtained with first dominant wavelength $\lambda d1$ selected from the range of 475-485 nm. Even more especially, the first dominant wavelength $\lambda d1$ may be selected from the range of 478-484 nm, such as about 480 nm.

The first light generating device further comprises a first luminescent material configured to convert part of the first light source light into first luminescent material light. Hence, part of the first light source stays unconverted and may be part of the first device light. Hence, the first device light comprises the first light source light and the first luminescent material light.

In specific embodiments, the first luminescent material comprises a phosphor having a full width half maximum of at least 25 nm (such as in embodiments at least 50 nm) and having a peak wavelength selected from the range of 590-640 nm. Even more especially, the first luminescent material may be configured to convert part of the first light source light into first luminescent material light having a first luminescent material dominant wavelength $\lambda dL1$ selected from the range of 575-638 nm. In embodiments, the first luminescent material dominant wavelength $\lambda dL1$ selected from the range of 575-630 nm. Even more especially, the first luminescent material dominant wavelength $\lambda dL1$ selected from the range of 575-612 nm, such as about 577-605 nm, or even about 577-599 nm. With FWHMs of above about 50 nm, the first luminescent material dominant wavelength $\lambda dL1$ may especially be below about 612 nm, whereas with FWHMs of 30 nm or smaller, the first luminescent material dominant wavelength $\lambda dL1$ may especially be below about 638 nm. In embodiments, the first luminescent material dominant wavelength $\lambda dL1$ may be obtained with a single luminescent material. In yet other embodiments, the first luminescent material dominant wavelength $\lambda dL1$ may be obtained with two or more first luminescent materials, such as e.g. a plurality of different types of quantum dots. In specific embodiments, however, first device light may essentially consist of a single type of first light sources, such as cyan LEDs, and a single type of first luminescent materials.

Especially good results may be obtained when the first dominant wavelength $\lambda d1$ is selected from the range of 478-484 nm and wherein the first luminescent material dominant wavelength $\lambda dL1$ selected from the range of 575-638 nm, such as about 577-605 nm, even more especially selected from the range of about 577-599 nm. This may provide a desired color point in a relative energy efficient way. To this end, e.g. divalent europium containing nitrides may be applied, as known in the art (examples are indicated below). Alternatively or additionally, tetravalent manganese doped fluorides such as $K_2SiF_6:Mn^{4+}$, or similar types of tetravalent manganese doped fluorides, can be applied. It especially appears that a combination of the first light source, such first luminescent material, and optionally one or more further first luminescent materials, such as of the cerium comprising garnet type, may be very useful for providing the first light generating device.

The term "first light source" may also refer to a plurality of essentially the same first light sources, such as solid state light sources from essentially the same bin. The term "first light source" may also refer to a plurality of different first light sources, though all complying with the herein indicated conditions. The term "first luminescent material" may also refer to a plurality of different luminescent materials.

Especially, the first device light is white light based on the color point using the 10° color matching functions.

In general, color points and correlated color temperatures are defined on the basis of 2° color matching functions (such as CIE 1931). As derived from the site https://www.konicaminolta.com/instruments/knowledge/color/part4/01.html the color sensitivity of the eye changes according to the angle of view (object size). The CIE originally defined the standard observer in 1931 using a 2 field of view, hence the name 2 Standard Observer. In 1964, the CIE defined an additional standard observer, this time based upon a 10° field of view; this is referred to as the 10 Supplementary Standard Observer. To give an idea of what a 2° field of view is like compared to a 10° field of view, at a viewing distance of 50 cm a 2° field of view would be a 1.7 cm circle while a 10° field of view at the same distance would be an 8.8 cm circle. The color matching functions are the tristimulus values of the equal-energy spectrum as a function of wavelength. These functions are intended to correspond to the sensitivity of the human eye. Separate sets of three color matching functions are specified for the 2° Standard Observer and 10° Supplementary Standard Observers.

Herein, CIE S 014-1/E:2006 see table 1 and 2, respectively, are therefore used.

In view of user perception, it appears more useful to define the color point of the first device light using the 10° color matching function. For comparing the color point of the first device light and the second device light, the color points using the 10° color matching function are herein applied. Hence, to compare these color points, both color points should be defined on the basis of 10° color matching functions. For comparing the color points of the second device light and the third device light, herein in general the color points using the 2° color matching function is applied. This also allows ascribing a correlated color temperature.

Note that the second device light and the third device light using the 2° color matching function are in specific embodiments white light. As the color point of the first device light and the second device light using the 10° color matching function are essentially the same (differing at maximum 0.03 for u' and/or at maximum 0.03 for v', such as at maximum 0.02 for u' and/or at maximum 0.02 for v', yet even more especially at maximum 0.01 for u' and/or at maximum 0.01 for v', yet even more especially at maximum 0.005 for u' and/or at maximum 0.005 for v'), de facto in embodiments the first device light is thus also white light and may be perceived as white light by the (10° Supplementary Standard) observer.

Especially assuming 2° color matching functions, the term "white light" herein, is known to the person skilled in the art. It especially relates to light having a correlated color temperature (CCT) between about 1800 K and 20000 K, such as between 2000 and 20000 K, especially 2700-20000 K, for general lighting especially in the range of about 2700 K and 6500 K. Yet further, in embodiments the correlated color temperature (CCT) is especially a color point within about 15 SDCM (standard deviation of color matching) from the BBL (black body locus), especially within about 10 SDCM from the BBL, even more especially within about 5 SDCM from the BBL.

Hence, the second device light is especially (such) white light. As, as indicated above the color points of the first device light and the second device light using the 10° color matching function are essentially the same, the first device light can also be indicated (in embodiments) as white light.

Further, the first device light has a first color point. Especially, in embodiments the color point is selected from the range of 0.18-0.24 for u' and 0.4-0.53 for v'(using 10° CMFs). More especially, u' may be selected from the range of 0.19-0.23, such as 0.195-0.22, more especially selected from the range of 0.195-0.205. More especially, v' may be selected from the range of 0.41-0.52, more especially selected from the range of 0.43-0.50, such as especially selected from the range of 0.46-0.47 (using 10° CMFs). The former range equals about 20,000-3,500 K in the u'v' CIE diagram of e.g. 1976.

Further, the first device light has a kind of first correlated color temperature Tc1. Hence, the first light generating device may be indicated as cool white light generating device.

The first light generating device may amongst others comprise a cyan LED as pump LED. Hence, the first light generating device may herein also be indicated as cyan LED or cyan PC LED.

The second light generating device is configured to generate second device light.

Especially, the second light generating device comprises a second light source configured to generate second light source light having a second dominant wavelength $\lambda d2$. The second light source especially comprises a solid state light source, such as an LED. Especially, the second dominant wavelength $\lambda d2$ is smaller than the first dominant wavelength $\lambda d1$. Hence, the first light source and the second light source are especially of different bins. In embodiments, $\lambda d1-\lambda d2 \geq 10$ nm.

The second light source may in embodiments be configured to generate visible light, especially blue light. Hence, in embodiments the second light source may especially be configured to generate first light source light having a second dominant wavelength $\lambda d2$ selected from the range of 430-470 nm (but at least smaller than the first dominant wavelength $\lambda d1$ (see also above)), such as at least 430 nm. In specific embodiments, $\lambda d2 \leq 465$ nm.

Alternatively or additionally, the second light source may in embodiments be configured to generate light having an even shorter (dominant) wavelength. Hence, in embodiments the second light source may especially be configured to generate first light source light having a second dominant wavelength $\lambda d2$ selected from the range of 380-430 nm.

The second light generating device further comprises a second luminescent material configured to convert at least part of the second light source light into second luminescent material light. Hence, at least part of the second light source light may stay unconverted and may be part of the second device light. Hence, the second device light comprises the second luminescent material light and optionally the second light source light. As indicated above, there may be two main embodiments. In first embodiments, the second light source may be configured to generate blue light. In such embodiments, one or more luminescent materials, may be used to convert part of the second light source light into second luminescent material light. In second embodiments, the second light source may be configured to generate light source light which has a dominant wavelength lower than the (blue) wavelength range of 430-470 nm. In such embodiments, especially the light source light may be fully converted into luminescent material light. Hence, in such second embodiments the second light generating device may especially comprise two or more different luminescent materials.

The term "second light source" may also refer to a plurality of essentially the same second light sources, such as solid state light sources from essentially the same bin. The term "second light source" may also refer to a plurality of different second light sources, though all complying with the herein indicated conditions. The term "second luminescent material" may also refer to a plurality of different luminescent materials.

Especially, the second device light is white light, as its color point, determined as x,y in the CIE 1931 color diagram (2° CMF), or u'v' in the CIE 1976 color diagram (in 2° CMF), is within 15 SDCM from the BBL, even more especially within about 10 SDCM from the BBL.

Further, the second device light has a second color point. Especially, in embodiments the second color point is selected from the range of 0.19-0.27 for u' and 0.42-0.54 for v' (in 2° CMF). More especially, second color point is selected from the range of 0.19-0.26 for u' and 0.43-0.53 for v' (in 2° CMF). For the second device light, it appears that the color point in 2° CMF or 10° CMF are substantially the same. Hence, in embodiments the second color point is selected from the range of about 0.19-0.27 for u' and about 0.42-0.54 for v' (in 10° CMF). More especially, second color point is selected from the range of about 0.19-0.26 for u' and about 0.43-0.53 for v' (in 10° CMF).

Further, the second device light may have a second correlated color temperature Tc2. Especially, in embodiments the second correlated color temperature Tc2 may be selected from the range of 2700-6500 K, especially at least about 3000 K, even more especially at least about 3300 K, such as at least 3400 K. More especially, the second correlated color temperature Tc2 may be at least 3500 K, such as even more especially at least about 4000 K. In yet further specific embodiments the second correlated color temperature Tc2 may be selected from the range of at least 4500 K, such as at least 5000 K, like selected from the range of 5000-6500 K. Hence, the second light generating device may be indicated as cool white light generating device.

As indicated above, the spectral power distributions of the first light source light and the second light source light differ. However, the color points may essentially be the same (based on 10° CMF). Hence, in embodiments the first color point and the second color point may differ at maximum 0.03 for u' and/or at maximum 0.03 for v' (based on 10° CMF), such as at maximum 0.01 for u' and/or at maximum 0.01 for v', even more especially at maximum 0.005 for u' and/or at maximum 0.005 for v' (using based on 10° CMF).

Hence, in embodiments the light generating system may comprise one or more first light generating devices and one or more second light generating devices, and no further types of light generating devices (that may contribute to the system light). Hence, in such embodiments the system light may essentially consist of the first device light and the second device light. In specific embodiments, however, the light generating system may further comprise a system, configured to control the system light. In such embodiments, it may be possible to control the spectral power distribution of the system light, e.g. by controlling the power to the first light generating device and the second light generating device (e.g. individually). Hence, in such embodiments the system light may essentially consist of one or more of the first device light and the second device light.

The term "controlling" and similar terms especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element. The controlling of the element can be done with a control system, which may also be indicated as "controller". The control system and the element may thus at least temporarily, or permanently, functionally be coupled. The element may comprise the control system. In embodiments, the control system and element may not be physically coupled. Control can be done via wired and/or wireless control. The term "control system" may also refer to a plurality of different control systems, which especially are functionally coupled, and of which e.g. one control system may be a master control system and one or more others may be slave control systems. A control system may comprise or may be functionally coupled to a user interface.

The control system may also be configured to receive and execute instructions form a remote control. In embodiments, the control system may be controlled via an App on a device, such as a portable device, like a Smartphone or I-phone, a tablet, etc. The device is thus not necessarily coupled to the lighting system, but may be (temporarily) functionally coupled to the lighting system.

Hence, in embodiments the control system may (also) be configured to be controlled by an App on a remote device. In such embodiments the control system of the lighting system may be a slave control system or control in a slave mode. For instance, the lighting system may be identifiable with a code, especially a unique code for the respective lighting system. The control system of the lighting system may be configured to be controlled by an external control system which has access to the lighting system on the basis of knowledge (input by a user interface of with an optical sensor (e.g. QR code reader) of the (unique) code. The lighting system may also comprise means for communicating with other systems or devices, such as on the basis of Bluetooth, WIFI, LiFi, ZigBee, BLE or WiMAX, or another wireless technology.

The system, or apparatus, or device may execute an action in a "mode" or "operation mode" or "mode of operation". Likewise, in a method an action or stage, or step may be executed in a "mode" or "operation mode" or "mode of operation" or "operational mode". The term "mode" may also be indicated as "controlling mode". This does not exclude that the system, or apparatus, or device may also be adapted for providing another controlling mode, or a plurality of other controlling modes. Likewise, this may not exclude that before executing the mode and/or after executing the mode one or more other modes may be executed.

However, in embodiments a control system may be available, that is adapted to provide at least the controlling mode. Would other modes be available, the choice of such modes may especially be executed via a user interface, though other options, like executing a mode in dependence of a sensor signal or a (time) scheme, may also be possible. The operation mode may in embodiments also refer to a system, or apparatus, or device, that can only operate in a single operation mode (i.e. "on", without further tunability).

Hence, in embodiments, the control system may control in dependence of one or more of an input signal of a user interface, a sensor signal (of a sensor), and a timer. The term "timer" may refer to a clock and/or a predetermined time scheme.

In yet further embodiments, the system may further comprise an input device selected from the group consisting of a user interface, a time device, and a sensor, wherein the control system may especially be configured to control a spectral power distribution of the system light in response to a signal of the input device.

The light generating system further comprises a third light generating device.

The third light generating device comprises a third light source configured to generate third light source light having a third dominant wavelength λd3. The third light source especially comprises a solid state light source, such as an LED. The third dominant wavelength λd3 is smaller than the first dominant wavelength λd1, and λd1-λd3≥10 nm. Hence, the first light source and the third light source are especially of different bins.

The third light source may in embodiments be configured to generate visible light, especially blue light. Hence, in embodiments the third light source may especially be configured to generate first light source light having a third dominant wavelength λd3 selected from the range of 430-470 nm (but at least smaller than the first dominant wavelength λd1 (see also above)), such as at least 430 nm. In specific embodiments, λd3≤465 nm.

Alternatively or additionally, the third light source may in embodiments be configured to generate light having an even shorter (dominant) wavelength. Hence, in embodiments the third light source may especially be configured to generate first light source light having a third dominant wavelength λd3 selected from the range of 380-430 nm.

The third light generating device further comprises a third luminescent material configured to convert at least part of the third light source light into third luminescent material light. Hence, at least part of the third light source light may stay unconverted and may be part of the third device light. Hence, the third device light comprises the third luminescent material light and optionally the third light source light. As indicated above, there may be two main embodiments. In first embodiments, the third light source may be configured to generate blue light. In such embodiments, one or more luminescent materials, may be used to convert part of the third light source light into third luminescent material light. In second embodiments, the third light source may be configured to generate light source light which has a dominant wavelength lower than the (blue) wavelength range of 430-470 nm. In such embodiments, especially the light source light may be fully converted into luminescent material light. Hence, in such third embodiments the third light generating device may especially comprise two or more different luminescent materials.

The term "third light source" may also refer to a plurality of essentially the same third light sources, such as solid state light sources from essentially the same bin. The term "third light source" may also refer to a plurality of different third light sources, though all complying with the herein indicated conditions. The term "third luminescent material" may also refer to a plurality of different luminescent materials.

Especially, the third device light is white light.

Further, the third device light has a third color point. Especially, in embodiments the color point is selected from the range of 0.22-0.30 for u' and 0.46-0.54 for v' (using 2° CMFs). More especially, in embodiments the color point is selected from the range of 0.23-0.29 for u' and 0.47-0.53 for v' (using 2° CMFs). For the third device light, it appears that the color point in 2° CMF or 10° CMF are substantially the same. Hence, in embodiments the color point is selected from the range of 0.22-0.30 for u' and 0.46-0.54 for v' (using 10° CMFs). More especially, in embodiments the color point is selected from the range of 0.23-0.29 for u' and 0.47-0.53 for v' (using 10° CMFs).

Assuming color points based on 2° CMFs $u'_2$ (the u' color coordinate of the second device light) is smaller than $u'_3$ (the color coordinate of the third device light). Especially, $u'_3$-$u'_2$≥0.01, especially $u'_3$-$u'_2$≥0.02, even more especially $u'_3$-$u'_2$≥0.03. Further, assuming color points based on 2° CMFs $v'_2$ (the v' color coordinate of the second device light) may be smaller than $v'_3$ (the color coordinate of the third device light). Especially, $v'_3$-$v'_2$≥0.01, especially $v'_3$-$v'_2$≥0.02, even more especially $v'_3$-$v'_2$≥0.03. In yet further specific embodiments, one or more (especially both) of the following applies: $u'_3$-$u'_2$≥0.04 and $v'_3$-$v'_2$≥0.04.

Further, the device light has a third correlated color temperature Tc3. Especially, in embodiments the third correlated color temperature Tc3 is selected from the range of 2000-4000 K, such as especially selected from the range of 2700-3500, such as up to about 3400 K.

Especially, Tc2-Tc3≥700 K, even more especially Tc2-Tc3≥800 K, yet even more especially Tc2-Tc3≥1000 K. Yet further, in specific embodiments, Tc2-Tc3≥1300 K. As indicated above, the correlated color temperatures are especially defined on the basis of 2° CMF.

Hence, the third light generating device may be indicated as warm white light generating device.

As can be derived from the above, in embodiments, the spectral power distributions of the first light source light and the third light source light differ.

Hence, in embodiments the light generating system may comprise one or more first light generating devices, one or more second light generating devices, and one or more third light generating devices, and no further types of light generating devices (that may contribute to the system light). Hence, in such embodiments the system light may essentially consist of the first device light, the second device light, and the third device light. In specific embodiments, however, the light generating system may further comprise a system (see also above), configured to control the system light. In such embodiments, it may be possible to control the spectral power distribution of the system light, e.g. by controlling the power to the first light generating device, the second light generating device, and the third light generating device (e.g. individually). Hence, in such embodiments the system light may essentially consist of one or more of the first device light, the second device light, and the third device light.

Here below, some further embodiments are described.

In specific embodiments, the first light source light has a first dominant wavelength λd1 selected from the range of 470-490 nm, the second light source light has a second dominant wavelength λd2 selected from the range of 390-470 nm, and the third light source light has a third dominant wavelength λd3 selected from the range of 390-470 nm. With such wavelength, in a relatively efficient way system light may be provided.

The term "light source" may refer to a semiconductor light-emitting device, such as a light emitting diode (LEDs), a resonant cavity light emitting diode (RCLED), a vertical cavity laser diode (VCSELs), an edge emitting laser, etc. The term "light source" may also refer to an organic light-emitting diode, such as a passive-matrix (PMOLED) or an active-matrix (AMOLED). In a specific embodiment, the light source comprises a solid state light source (such as a LED or laser diode). In an embodiment, the light source comprises a LED (light emitting diode). The term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of semiconductor light sources may be configured on the same substrate. In embodiments, a COB is a multi LED chip configured together as a single lighting module. The term "light source" may also relate to a plurality of (essentially identical (or different)) light sources, such as 2-2000 solid state light sources. In embodiments, the light source may comprise one or more micro-optical elements (array of micro lenses) downstream of a single solid state light source, such as a LED, or downstream of a plurality of solid state light sources (i.e. e.g. shared by multiple LEDs). In embodiments, the light source may comprise a LED with on-chip optics. In embodiments, the light source comprises a pixelated single LEDs (with or without optics) (offering in embodiments on-chip beam steering).

The phrases "different light sources" or "a plurality of different light sources", and similar phrases, may in embodiments refer to a plurality of solid state light sources selected from at least two different bins. Likewise, the phrases "identical light sources" or "a plurality of same light sources", and similar phrases, may in embodiments refer to a plurality of solid state light sources selected from the same bin.

In specific embodiments, of the luminescent materials (210,220,230) comprise each phosphor, each configured to provide emission with each having a full width half maximum of at least 25 nm. For instance, one or more of the first luminescent material, the second luminescent material and the third luminescent material may comprise quantum dots.

In other embodiments, the second luminescent material and/or the third luminescent material comprise phosphors configured to provide luminescent material light (221,231) having a full width half maximum of at least 40 nm. Hence, in embodiments the second luminescent material light may have a FWHM of at least 40 nm. Alternatively or additionally, in embodiments the third luminescent material light may have a FWHM of at least 40 nm.

In embodiments, the second luminescent material comprises one or more of a cerium comprising garnet type luminescent material and a divalent europium based nitride material. Especially, both may be comprised by the second luminescent material. Alternatively or additionally, in embodiments, the third luminescent material comprises one or more of a cerium comprising garnet type luminescent material and a divalent europium based nitride material. Especially, both may be comprised by the third luminescent material. In yet further embodiments, the third luminescent material may (additionally) comprise a narrow band red emitting phosphor based on $Mn^{4+}$.

When a luminescent material is applied herein, the luminescent material is especially configured downstream of a light source, such as in the above embodiment the white light emitting solid state light source. The light source may thus in embodiments be configured upstream of the luminescent material, with the luminescent material being configured to convert at least part of the light source light. The terms "upstream" and "downstream" relate to an arrangement of items or features relative to the propagation of the light from a light generating means (here the especially the light source), wherein relative to a first position within a beam of light from the light generating means, a second position in the beam of light closer to the light generating means is "upstream", and a third position within the beam of light further away from the light generating means is "downstream".

For green, yellow, orange, and/or red emitting luminescent material, e.g. inorganic luminescent material with activators or active species may be applied. Relevant active species may e.g. $Eu^{2+}$ or $Ce^{3+}$. Other active species may be quantum dots. Yet other active species may be organic luminescent dyes.

In embodiments, luminescent materials may be selected from garnets and nitrides, especially doped with trivalent cerium or divalent europium, respectively. Embodiments of garnets especially include $A_3B_5O_{12}$ garnets, wherein A comprises at least yttrium or lutetium and wherein B comprises at least aluminum. Such garnets may be doped with cerium (Ce), with praseodymium (Pr) or a combination of cerium and praseodymium; especially however with Ce. Especially, B comprises aluminum (Al), however, B may also partly comprise gallium (Ga) and/or scandium (Sc) and/or indium (In), especially up to about 20% of Al, more especially up to about 10% of Al (i.e. the B ions essentially consist of 90 or more mole % of Al and 10 or less mole % of one or more of Ga, Sc and In); B may especially comprise up to about 10% gallium. In another variant, B and O may at least partly be replaced by Si and N. The element A may especially be selected from the group consisting of yttrium (Y), gadolinium (Gd), terbium (Tb) and lutetium (Lu). Further, Gd and/or Tb are especially only present up to an amount of about 20% of A. In a specific embodiment, the garnet luminescent material comprises $(Y_{1-x}Lu_x)_3B_5O_{12}$:Ce, wherein x is equal to or larger than 0 and equal to or smaller than 1.

The term ":Ce", indicates that part of the metal ions (i.e. in the garnets: part of the "A" ions) in the luminescent material is replaced by Ce. For instance, in the case of $(Y_{1-x}Lu_x)_3Al_5O_{12}$:Ce, part of Y and/or Lu is replaced by Ce. This is known to the person skilled in the art. Ce will replace A in general for not more than 10%; in general, the Ce concentration will be in the range of 0.1 to 4%, especially 0.1 to 2% (relative to A). Assuming 1% Ce and 10% Y, the full correct formula could be $(Y_{0.1}Lu_{0.89}Ce_{0.01})_3Al_5O_{12}$.

Ce in garnets is substantially or only in the trivalent state, as is known to the person skilled in the art.

In embodiments, a red luminescent material may comprise one or more materials selected from the group consisting of (Ba,Sr,Ca)S:Eu, (Ba,Sr,Ca)AlSiN$_3$:Eu and (Ba,Sr,Ca)$_2$Si$_5$N$_8$:Eu. In these compounds, europium (Eu) is substantially or only divalent, and replaces one or more of the indicated divalent cations. In general, Eu will not be present in amounts larger than 10% of the cation; its presence will especially be in the range of about 0.5 to 10%, more especially in the range of about 0.5 to 5% relative to the cation(s) it replaces. The term ":Eu", indicates that part of the metal ions is replaced by Eu (in these examples by $Eu^{2+}$). For instance, assuming 2% Eu in CaAlSiN$_3$:Eu, the correct formula could be $(Ca_{0.98}Eu_{0.02})AlSiN_3$. Divalent europium will in general replace divalent cations, such as the above divalent alkaline earth cations, especially Ca, Sr or Ba.

The material (Ba,Sr,Ca)S:Eu can also be indicated as MS:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca).

Further, the material (Ba,Sr,Ca)$_2$Si$_5$N$_8$:Eu can also be indicated as M$_2$Si$_5$N$_8$:Eu, wherein M is one or more elements selected from the group consisting of barium (Ba), strontium (Sr) and calcium (Ca); especially, M comprises in this compound Sr and/or Ba. In a further specific embodiment, M consists of Sr and/or Ba (not taking into account the presence of Eu), especially 50 to 100%, more especially 50 to 90% Ba and 50 to 0%, especially 50 to 10% Sr, such as $Ba_{1.5}Sr_{0.5}Si_5N_8$:Eu (i.e. 75% Ba; 25% Sr). Here, Eu is introduced and replaces at least part of M, i.e. one or more of Ba, Sr, and Ca).

Likewise, the material (Ba,Sr,Ca)AlSiN$_3$:Eu can also be indicated as MAlSiN$_3$:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca).

Eu in the above indicated luminescent materials is substantially or only in the divalent state, as is known to the person skilled in the art.

The garnet type luminescent material may especially be applied as second and/or third luminescent material.

The term "luminescent material" herein especially relates to inorganic luminescent materials, which are also sometimes indicated as phosphors. These terms are known to the person skilled in the art.

The term "luminescent material" especially refers to a material that can convert first radiation, especially one or more of UV radiation and blue radiation, into second radiation. In general, the first radiation and second radiation have different spectral power distributions. Hence, instead of the term "luminescent material", also the terms "luminescent converter" or "converter" may be applied. In general, the second radiation has a spectral power distribution at larger wavelengths than the first radiation, which is the case in the so-called down-conversion. In specific embodiments, however the second radiation has a spectral power distribution with intensity at smaller wavelengths than the first radiation, which is the case in the so-called up-conversion. In embodiments, the "luminescent material" may especially refer to a material that can convert radiation into e.g. visible and/or infrared light. For instance, in embodiments the luminescent material may be able to convert one or more of UV radiation and blue radiation, into visible light. The luminescent material may in specific embodiments also convert radiation into infrared radiation (IR). Hence, upon excitation with radiation, the luminescent material emits radiation. In general, the luminescent material will be a down converter, i.e. radiation of a smaller wavelength is converted into radiation with a larger wavelength ($\lambda_{ex}<\lambda_{em}$), though in specific embodiments the luminescent material may comprise down-converter luminescent material, i.e. radiation of a larger wavelength is converted into radiation with a smaller wavelength ($\lambda_{ex}>\lambda_{em}$). In embodiments, the term "luminescence" may refer to phosphorescence. In embodiments, the term "luminescence" may also refer to fluorescence. Instead of the term "luminescence", also the term "emission" may be applied. Hence, the terms "first radiation" and "second radiation" may refer to excitation radiation and emission (radiation), respectively. Likewise, the term "luminescent material" may in embodiments refer to phosphorescence and/or fluorescence. The term "luminescent material" may also refer to a plurality of different luminescent materials.

As indicated above, in specific embodiments the light generating system may further optionally comprise a control system configured to control the first light generating device and the second light generating device. As the system may also comprise a third light generating device, in specific embodiments the light generating system may further comprise a control system configured to control the first light generating device, the second light generating device, and the third light generating device. Especially, in embodiments the control system may be configured to individually control two or more of the first light generating device, second light generating device, and the third light generating device. In this way, the spectral power distribution can be controlled, and concomitantly the MDER value may be controlled.

Further, with the present solution color differences between the cyan based light source and the second light generating device are substantially removed, as both may substantially emit device light with essentially the same color point (using 10° CMFs). Hence, the present invention also allows a simplification in the sense that the first light generation device and the second light generating device are controlled as set. Hence, in specific embodiments the control system may be configured to individually control (a) a set comprising the first light generating device and the second light generating device, and (b) the third light generating device.

For instance, this may also allow arranging the first light generating device and the second light generation device in a first string, and the third light generating device in a second string.

Hence, the light generating system comprises (i) a first LED string comprising one or more first light generating devices and one or more second light generating devices and (ii) a second LED string comprising one or more third light generating devices.

As indicated above, especially the light sources (10,20, 30) comprise solid state light sources.

Especially, in embodiments the number n1 of first light generating devices plus the number n2 of second light generating devices may essentially be the same as the number n3 of third light generating devices. Hence, in specific embodiments (n1+n2)/n3=1. Then number n1 of first light generating devices plus the number n2 of second light generating devices in the first string may be chosen in dependence of e.g. the type of application. Especially, in embodiments a ratio of (a) number n1 of first light generating devices and (b) number n2 of second light generating devices with 0.05≤n1/n2≤20, though other values may also be possible.

Note that in specific embodiments the term "first string" may also refer to a plurality of electrically parallel arranged first strings. Note that in specific embodiments the term "second string" may also refer to a plurality of electrically parallel arranged second strings.

With the present invention, system light may be provided with a relatively high MDER. Further, this may be provided in a way that the color difference between a white LED and a cyan LED may not be an issue (see also above).

With respect to the MDER value, in an operational mode of the light generation system the system light may have an MDER value selected from the range of at least 0.45, even more especially at least 0.65, wherein MDER is defined as:

$$MDER = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3a)}$$

wherein SPD($\lambda$) is the spectral power distribution of the system light, m($\lambda$) is the melanopic sensitivity function, the V($\lambda$) is the photopic luminosity function.

Further, in specific embodiments, in an operational mode of the light generation system the system light may have a CRI of at least 80. Yet further, in specific embodiments, in an operational mode of the light generation system the system light may have an R9 value of at least 50. Hence, in specific embodiments, in an operational mode of the light generation system the system light may have an MDER of at least 0.45, a CRI of at least 80, such as at least 85, and an R9 of at least 50. Especially, the system light may have an MDER of at least 0.65.

For instance, in embodiments the control system may be configured to control in an operational mode the spectral power distribution of the system light while maintaining a predefined MDER value. The term "predefined MDER value" may refer to a value or to a range of values. Especially, it may refer to a subset of an MDER range of 0.45-1.3, such as in the range of 0.65-0.89. MDER values larger than 1.3 may also be possible, but this may result in a less desirable CRI.

As indicated above, in embodiments the light generating system may further comprise an input device selected from the group consisting of a user interface, a time device, and a sensor. Especially, the control system (see also above) may be configured to control a spectral power distribution of the system light in response to a signal of the input device. For instance, at higher daylight levels, the system light may be reduced. For instance, later in the day, such as during the evening, the MDER value may be reduced. In embodiments, the MDER value may be made dependent upon the daylight level (and or the time of the day). Other embodiments may also be possible. Hence, especially the control system may be configured to control the spectral power distribution of the system light of the light generating system, such as the light generating system wherein the system comprises (i) a first LED string comprising one or more first light generating devices and one or more second light generating devices and (ii) a second LED string comprising one or more third light generating devices, such as in embodiments a light generating system comprising (i) a first LED string comprising one or more first light generating devices and one or more second light generating devices and (ii) a second LED string comprising one or more third light generating devices.

In yet a further aspect, the invention provides a lamp or a luminaire comprising the light generating system as defined herein. The luminaire may further comprise a housing, optical elements, louvres, etc. etc. . . . . The lamp or luminaire may further comprise a housing enclosing the first light generating device, the second light generating device, and the optional third light generating device. The lamp or luminaire may comprise a light window in the housing or a housing opening, through which the system light may escape from the housing.

The light generating system may be part of or may be applied in e.g. office lighting systems, household application systems, shop lighting systems, home lighting systems, accent lighting systems, spot lighting systems, theater lighting systems, fiber-optics application systems, projection systems, self-lit display systems, pixelated display systems, segmented display systems, warning sign systems, medical lighting application systems, indicator sign systems, decorative lighting systems, portable systems, automotive applications, (outdoor) road lighting systems, urban lighting systems, green house lighting systems, horticulture lighting, digital projection, or LCD backlighting.

The terms "blue light" or "blue emission" especially relates to light having a wavelength in the range of about 440-495 nm (including some violet and cyan hues). The terms "green light" or "green emission" especially relate to light having a wavelength in the range of about 495-570 nm. The terms "yellow light" or "yellow emission" especially relate to light having a wavelength in the range of about 570-590 nm. The terms "orange light" or "orange emission" especially relate to light having a wavelength in the range of about 590-620 nm. The terms "red light" or "red emission" especially relate to light having a wavelength in the range of about 620-780 nm. The term "pink light" or "pink emission" refers to light having a blue and a red component.

The terms "visible", "visible light" or "visible emission" and similar terms refer to light having one or more wavelengths in the range of about 380-780 nm.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily to scale.

DETAILED DESCRIPTION OF THE EMBODIMENTS

In embodiments a direct cyan emitter may be replaced by a cyan pumped phosphor converted LED. The combination of cyan and a red phosphor can be used to generate cool white color points (e.g. 6500K). These LEDs may then be used in a 2 channel tunable system. For instance, the system may use warm white LEDs in one string and a combination of cyan-pumped LEDs and cool white LEDs in the second string. Especially, the color point of the cool white LED and the cyan-pumped LED may be essentially identical. The two cool white LEDs are spectrally extremely different (see FIG. 1), resulting in e.g. a CRI difference of >60. However, as the color points may essentially be the same they may appear the same when looking at them in on-state and may not give color shadows, even when combined with lenses. Since both types of the LEDs in the cyan enhanced string may have essentially identical color points, there may be more freedom to tune the cyan content in the final spectrum (e.g. 0-12 LEDs in steps of 1 can be varied, without problems with color inhomogeneity; see FIGS. 2-3). Note that not necessarily 12 LEDs are applied. Other numbers may also be possible.

Figure 1:
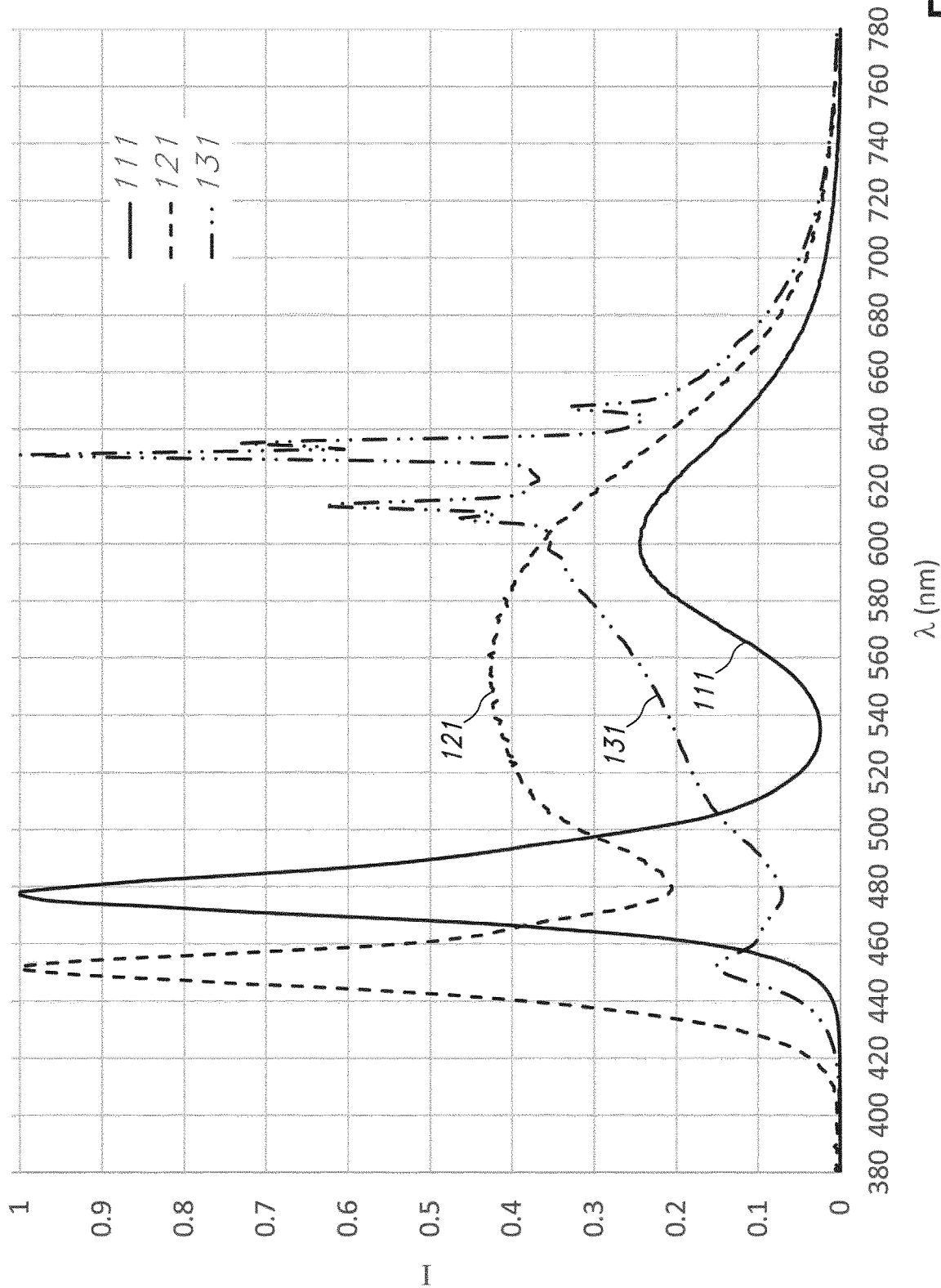
FIG. 1 shows spectral power distributions (normalized) of embodiments of first device light 111, second device light 121, and third device light 131.

Referring to FIG. 1, in embodiments the first light source light 11 may have a first dominant wavelength λd1 selected from the range of 470-490 nm. Further, the second light source light 21 may have a second dominant wavelength λd2 selected from the range of 390-470 nm. Yet further, the third light source light 31 may have a third dominant wavelength λd3 selected from the range of 390-470 nm. As also shown, in these embodiments, each of the luminescent materials comprises a phosphor, each configured to provide emission having a full width half maximum of at least 25 nm. In specific embodiments, the second luminescent material and the third luminescent material comprise phosphors configured to provide luminescent material light 221,231 having a full width half maximum of at least 40 nm. The third luminescent material may comprise a narrow band red emitting phosphor based on $Mn^{4+}$. However, also the second luminescent material may comprise a narrow band red emitting phosphor based on $Mn^{4+}$. Yet further, in specific embodiments also the first luminescent material may comprise a narrow band red emitting phosphor based on $Mn^{4+}$. In embodiments, however, the first luminescent material, the second luminescent material and the third luminescent material may comprise at least two different material compositions. This may relate to different weight ratios and/or different types of luminescent materials.

Figure 2:
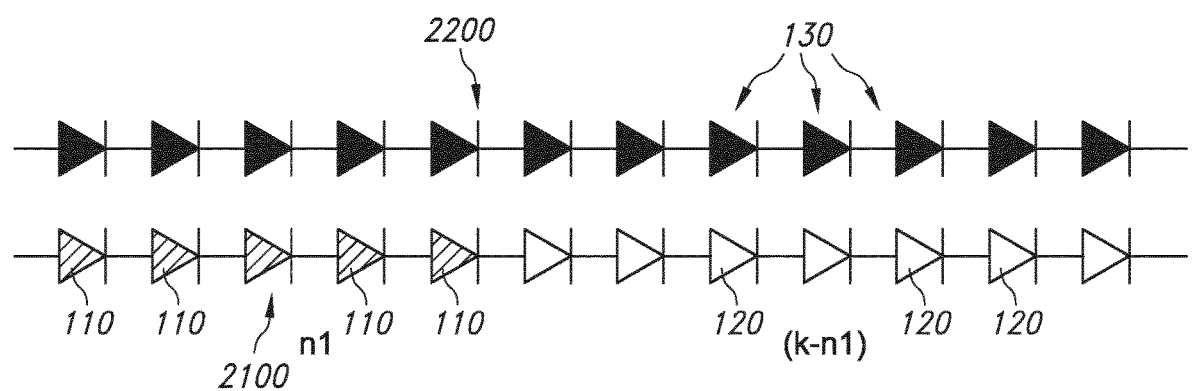
FIG. 2 schematically depicts an embodiment of the light generating device comprising two strings of LEDs.

FIG. 2 schematically depicts an embodiment of a possible combination of strings.

In specific embodiments, see also FIG. 2, the light generating system 1000 may comprise (i) a first LED string 2100 comprising one or more first light generating devices 110 and one or more second light generating devices 120 and (ii) a second LED string 2200 comprising one or more third light generating devices 130, wherein the light sources comprise solid state light sources. In embodiments, in one of the strings there may be a ratio of a number n1 of first light generating devices 110 and a number n2 of second light generating devices 120 of 0.05≤n1/n2≤20. In these embodiments, both strings have k light generating devices. Hence, in this embodiment k−n1=n2 second light generating devices 120. The second string 2200 has k third light generating devices 130.

Figure 3:
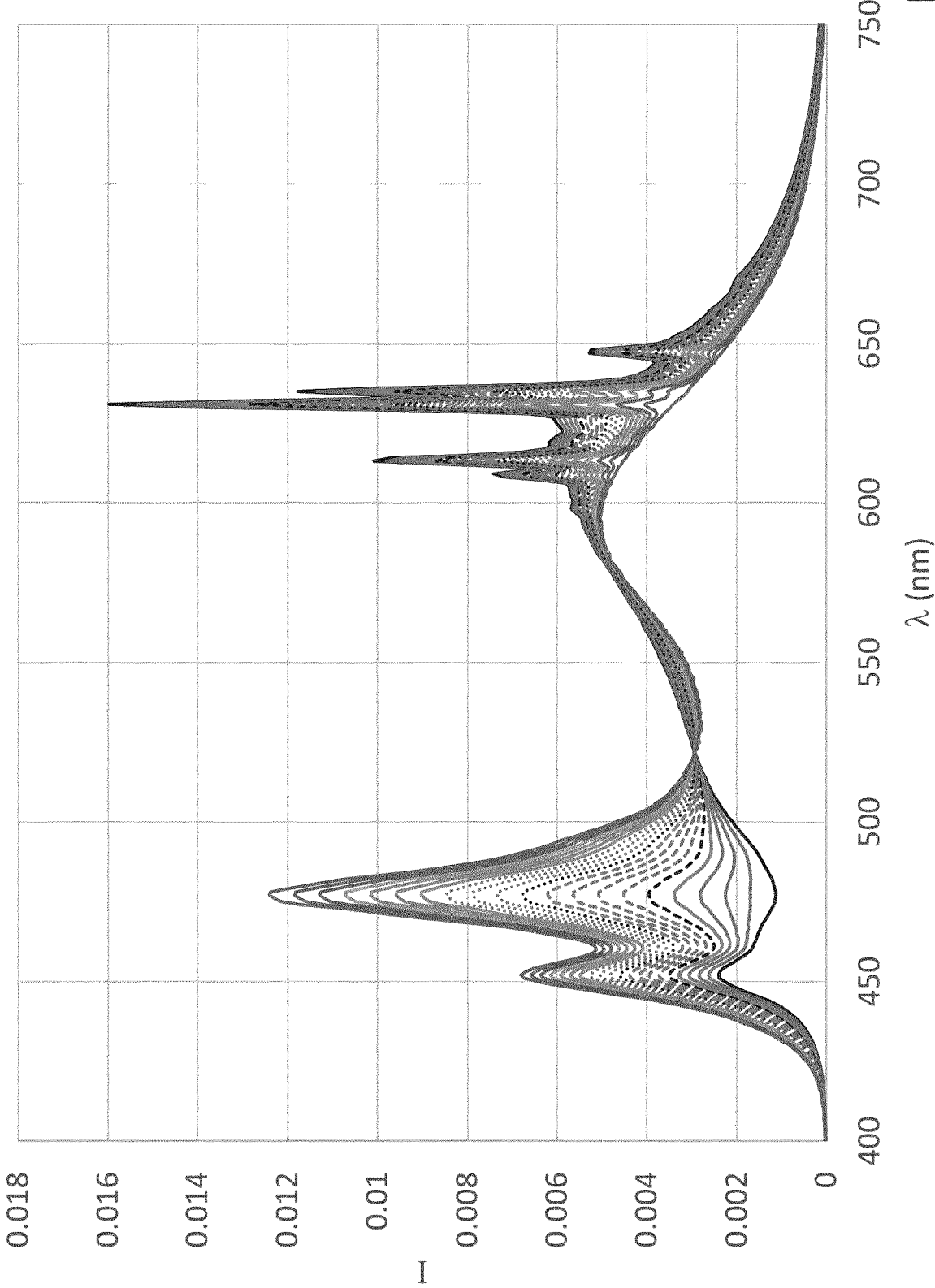
FIG. 3 shows shifts in spectral power distributions as function of different number of first light generating devices and second light generating devices in one of the strings.

The performance of a tunable system was calculated using different LED combinations. The warm white LED used in these cases has a CRI>90 and a CCT of 3000 K). FIG. 3 shows different spectra achievable for different n1/n2 for the same LED types (i.e. 1 cyan DWL—red phosphor combination for light generating device 110; see also FIG. 1).

Several combinations of cyan DWL (dominant wavelength) and red phosphor were used in the calculations. The choice of the DWL of the cyan LED and the thickness i.e. extent of conversion of the red phosphor were adjusted to the choice of the red phosphor in order to stay close to the 6500K point on the BBL (here defined using 10° CMFs).

The performance of several different LED combinations was evaluated in the above described method, in particular making the cyan enhanced 6500K LED by different cyan DWL—red phosphor combinations: cyan DWLs 486, 487 and 489 nm with red phosphors PP 611, 620, 628 and 639 nm respectively. Here, DWL indicates the dominant wavelength and PP indicates the peak position. Amongst others, it appears that a system with CRI>80 and melanopic-DER>1 at 5000K is feasible, and that a system with CRI>80 and MDER of ~0.9 at 4200K is feasible.

Figure 4:
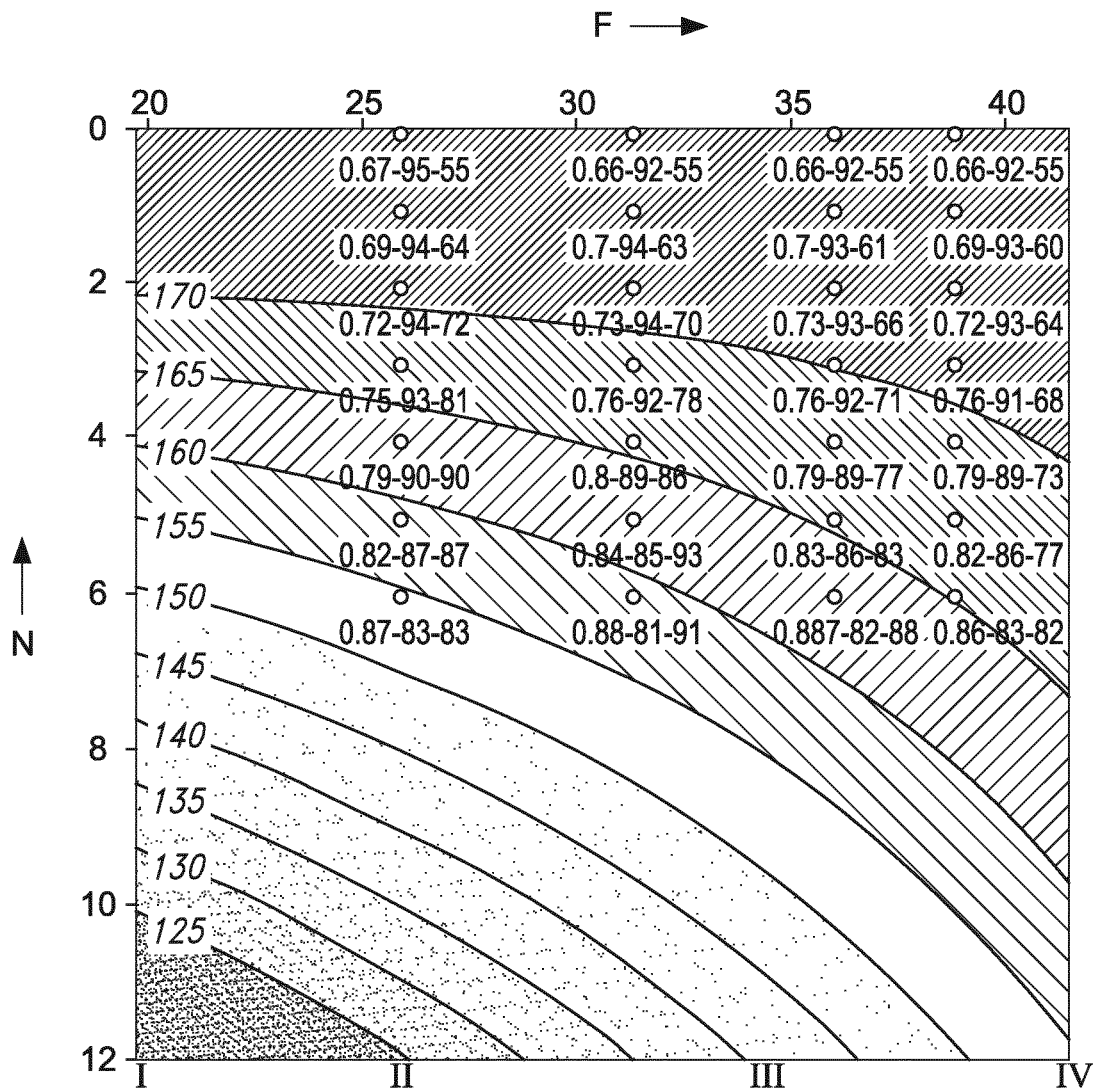
FIG. 4 shows the result of calculations wherein shadings indicate the efficiency of power-balance luminaire (4400 lumen, LOR=0.9, 4000K) as a function of the number of cyan-red LEDs in the cool white channel (horizontal axis) and the flux at reference conditions of the cyan-red LED (left vertical axis); the labels on the bottom give the corresponding red phosphor used in the cyan-red LEDs (see table 1). The white dots represent the situations were CRI is above 80. The data labels give the melanopic-DER, CRI and R9.

The performance of the different options was calculated. Using a longer DWL cyan LED may require a deeper red phosphor to target the BBL. In principle a longer wavelength cyan LED fits better in the melanopic stimulation curve. Note that the amount of cyan light in the cyan-red spectrum decreases significantly, as we need to generate more red light to target 'white' light. These different cyan LEDs were used in a tunable system. The efficiency as a function of CCT and the number of cyan-red LEDs in the cool white string (total length=12) was calculated. The shorter the peak wavelength of the red phosphor in the cyan LED, the better the efficiency of the system (as expected). Surprisingly, the MDER of the system does not substantially depend on the choice of the cyan-red phosphor combination (FIG. 4). For melanopic-DER, the choice of the cyan-red LED may be less important, for system efficiency it is best to choose the shortest possible red phosphor (and shorter DWL cyan LED).

Hence, combining cyan pumped LEDs and blue pumped LEDs with the same color as the second channel may allow to generate tunable systems with a large tuning range.

In FIG. 4 shadings indicate the efficiency of power-balance luminaire (4400 lumen, LOR=0.9, 4000K) as a function of the number N of cyan-red LEDs in the cool white channel (vertical axis) and the flux (F) at reference conditions of the cyan-red LED (top horizontal axis); the labels on the bottom give the corresponding red phosphor used in the cyan-red LEDs, as indicated in the table below. From left to right the peak position decreases. The white dots represent the situations were CRI is above 80. The data labels give the melanopic-DER, CRI and R9.

| DWL LED (nm) | Red phosphor peak position (nm) | DWL red phosphor (nm) | Indication in FIG. 4 | CE (max) | Fraction Cyan left | Relative flux |
|---|---|---|---|---|---|---|
| 480 | 607 | 591 | IV | 199.3 | 0.509 | 41.5 |
| 480 | 611 | 593 |  | 186.5 | 0.492 | 38.8 |
| 481 | 620 | 596 |  | 174.8 | 0.487 | 36 |
| 483 | 622 | 599 | III | 169.6 | 0.497 | 34.3 |
| 483 | 628 | 602 |  | 154.6 | 0.471 | 31.3 |
| 484 | 639 | 606 | II | 129.2 | 0.405 | 25.9 |
| 487 | 660 | 613 | I | 101 | 0.334 | 19.7 |

Certainly for the CRI>80 requirement, in the CCT region of interest (3000-5000K), the maximum MDER values can be achieved with all the cyan DWL—red phosphor combinations. But the LED efficiencies are different. The combination 480 nm-611 nm may provide the highest efficiency.

It was learned from perception testing that it is better to match the color points using 10° CMF.

Amongst others, the invention can also be used for light sources for static high melanopic stimulation. Then the cyan pumped white LED color point should be targeted at the same color point of the white LEDs for this static solution, most probably more likely around 4000 K.

Amongst others, the invention also provides a white light source with tunable melanopic stimulation i.e. high MDER at high CCT and low/normal MDER at low CCT by combining a string of warm white LEDs (string 1) and a second string consisting of cyan pumped LEDs combined with (blue pumped) cool white LEDs, in which: (a) the color point of the two LEDs in the cool white string are essentially identical; and (b) the number of cyan pumped LEDs/string may in specific embodiments e.g. be >0 and <8. Further, especially (c) the difference in CRI between the cyan pumped LED and the cool white LED is >60.

Figure 5A:
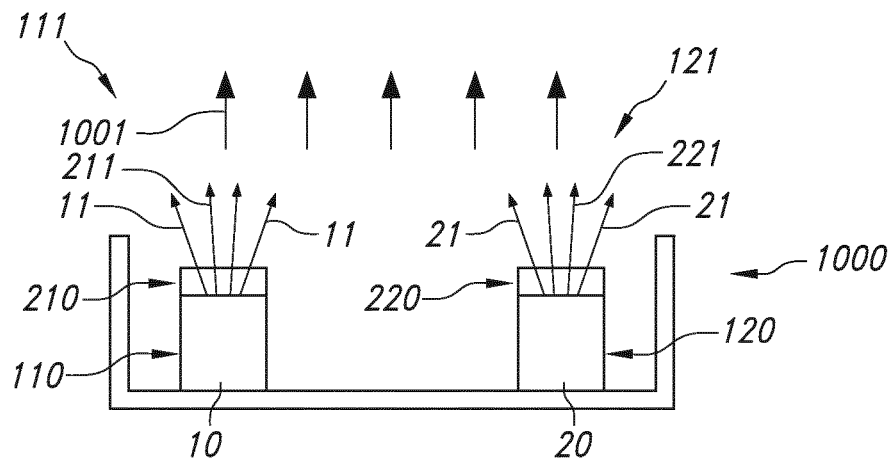
FIGS. 5a-5d schematically depict a number of embodiments.

FIG. 5*a* schematically depicts an embodiment of a light generating system 1000 configured to generate system light 1001. The light generating system 1000 comprises a first light generating device 110 and a second light generating device 120.

The first light generating device 110 is configured to generate first device light 111. The first light generating device 110 comprises a first light source 10 configured to generate first light source light 11 having a first dominant wavelength λd1 (e.g. selected from the range of 470-500 nm), and a first luminescent material 210 configured to convert part of the first light source light 11 into first luminescent material light 211.

The first device light 111 comprises the first light source light 11 and the first luminescent material light 211.

Especially, the first device light 111 may be white light having. Further, the first device light 111 has a first color point. Yet further, the first device light 111 may have a first correlated color temperature Tc1.

The first light generating device may especially be a cyan PC LED providing cool white.

The second light generating device 120 is configured to generate second device light 121. The second light generating device 120 comprises a second light source 20 configured to generate second light source light 21 having a second dominant wavelength λd2, and a second luminescent material 220 configured to convert at least part of the second light source light 21 into second luminescent material light 221. The second device light 121 comprises the second luminescent material light 221 and optionally the second light source light 21.

Especially, the second device light 121 may be white light. The second device light 121 has a second color point. The second device light 121 may have a second correlated color temperature Tc2.

Especially, λd1-λd2≥10 nm. In embodiments, λd2≤465 nm.

As also shown in FIG. 1, the spectral power distributions of the first light source light 11 and the second light source light 21 differ.

Especially, the first color point and the second color point differ at maximum 0.03 for u' and/or at maximum 0.03 for v', such as at maximum 0.01 for u' and/or at maximum 0.01 for v', especially using the 10° color matching functions according to CIE S 014-1/E:2006 see table 2.

The second light generating device especially comprises a PC LED comprising a blue solid state light source (pump), configured to provide cool white light.

In embodiments, see also FIG. 1, the first dominant wavelength λd1 is selected from the range of 478-484 nm. In embodiments, see also FIG. 1, the first luminescent material 210 is configured to convert part of the first light source light 11 into first luminescent material light 211 having a first luminescent material dominant wavelength λdL1 selected from the range of 575-638 nm.

The lighting system light 1001 may in an operational mode especially comprise both the first device light 111 and the second device light 121. Hence, lighting system light 1001 may in an operational mode especially comprise first light source light 11, first luminescent material light 211, second light source light 21, and second luminescent material light 221.

Figure 5B:
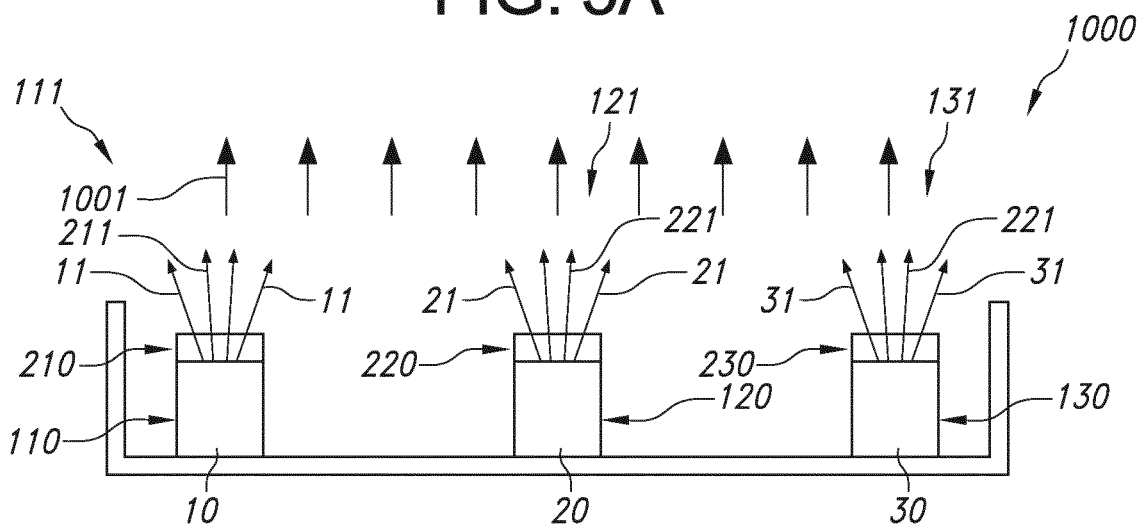

FIG. 5b schematically depicts an embodiment of the light generating system 1000 further comprising a third light generating device 130.

The third light generating device 130 is configured to generate third device light 131. The third light generating device 130 comprises a third light source 30 configured to generate third light source light 31 having a third dominant wavelength λd3, and a third luminescent material 230 configured to convert at least part of the third light source light 31 into third luminescent material light 231

The third device light 131 comprises the third luminescent material light 231 and optionally the third light source light 31.

The third device light 131 may be white light. The third device light 131 has a third color point. The third device light 131 may have a third correlated color temperature Tc3.

Especially, in embodiments, λd1-λd3≥10 nm. In specific embodiments, λd3≤465 nm.

As can also be seen in FIG. 1, the spectral power distributions of the first light source light 11 and the third light source light 31 differ.

Especially, the system light 1001 comprises one or more of the first device light 111, the second device light 121, and third device light 131.

The lighting system light 1001 may in an operational mode especially comprise all of the first device light 111, the second device light 121 and the third device light 131. Hence, lighting system light 1001 may in an operational mode especially comprise first light source light 11, first luminescent material light 211, second light source light 21, second luminescent material light 221, third light source light 31 and third luminescent material light 231. However, other embodiments may also be possible.

In specific embodiments, Tc2-Tc3≥1000K.

The third light generating device especially comprises a PC LED comprising a blue solid state light source (pump) configured to provide warm white light.

Figure 5C:
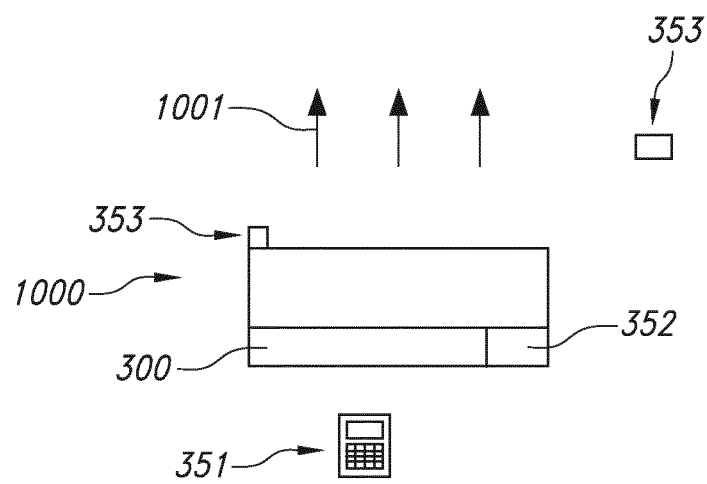

As schematically depicted in FIG. 5c, the light generating system 1000 may further comprising a control system 300 configured to control the first light generating device 110, the second light generating device 120, and the optional third light generating device 130.

In embodiments, the control system 300 may be configured to individually control (a) a set comprising the first light generating device 110 and the second light generating device 120, and (b) the third light generating device 130; see also FIG. 2.

The light generating system 1000 may further comprise an input device 350 selected from the group consisting of a user interface 351, a time device 352, and one or more sensors 353.

The control system may especially be configured to control a spectral power distribution of the system light 1001 in response to a signal of the input device 350.

Figure 5D:
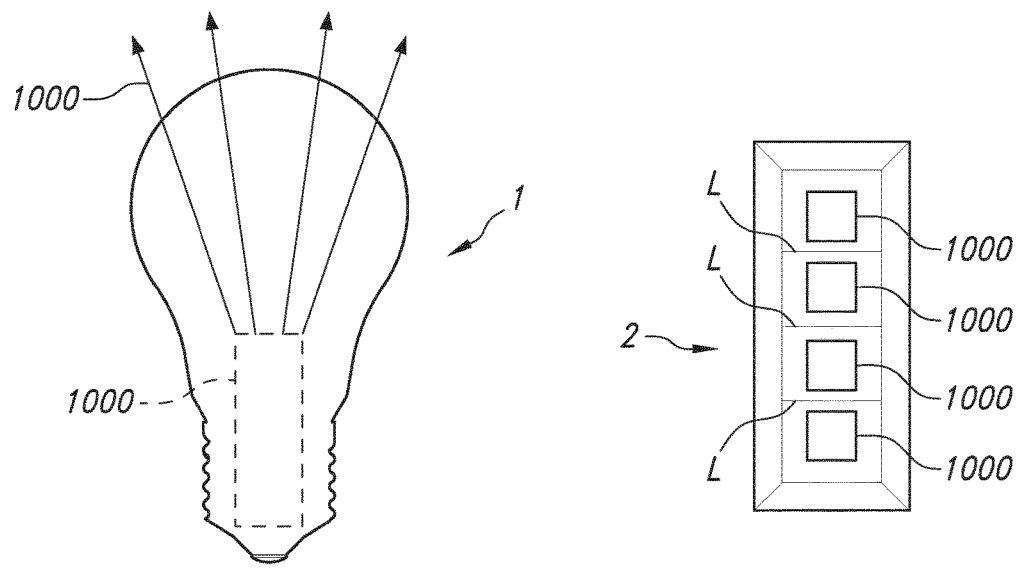

FIG. 5d schematically depict embodiments of a lamp 1 (embodiment I) or a luminaire 2 (embodiment II) comprising the light generating system 1000. In embodiment II, reference L indicates louvers. However, other embodiments may of course also be possible.

Figure 6:
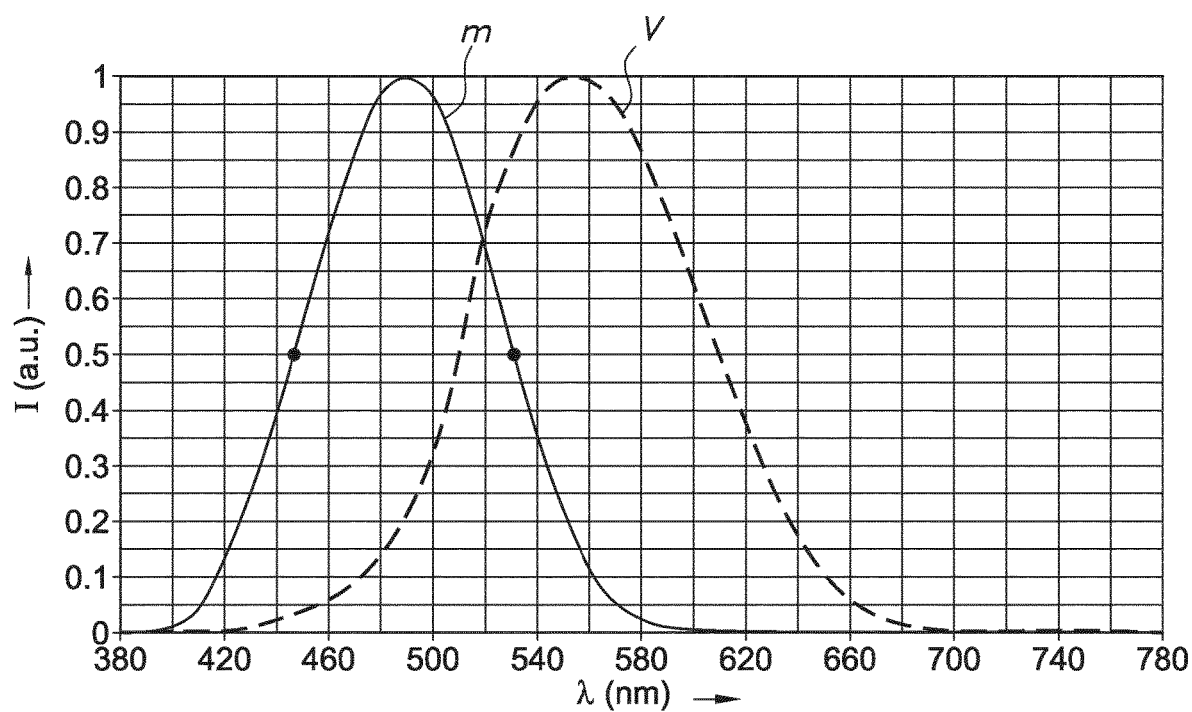
FIG. 6 shows the relative melanopic (m) (i.e. $m(\lambda)$) and $V(\lambda)$ human eye sensitivity functions.

FIG. 6 shows the relative melanopic (m) (i.e. m(λ)) and photopic (V(λ)) human eye sensitivity functions. The maximum sensitivity for the melanopic function is at 490 nm, the full width half maximum values are at 447 nm and 531 nm, see also the accompanying table for the melanopic and photopic human eye sensitivity functions:

| | Photopic | Melanopic |
| --- | --- | --- |
| 380 | 0.000039 | 0.000918 |
| 381 | 4.28264E−05 | 0.001033 |
| 382 | 4.69146E−05 | 0.001163 |
| 383 | 5.15896E−05 | 0.00131 |
| 384 | 5.71764E−05 | 0.001477 |
| 385 | 0.000064 | 0.001667 |
| 386 | 7.23442E−05 | 0.001883 |
| 387 | 8.22122E−05 | 0.002129 |
| 388 | 9.35082E−05 | 0.00241 |

|     | Photopic    | Melanopic |
| --- | ----------- | --------- |
| 389 | 0.000106136 | 0.002729  |
| 390 | 0.00012     | 0.003094  |
| 391 | 0.000134984 | 0.003512  |
| 392 | 0.000151492 | 0.003989  |
| 393 | 0.000170208 | 0.004536  |
| 394 | 0.000191816 | 0.005162  |
| 395 | 0.000217    | 0.00588   |
| 396 | 0.000246907 | 0.006705  |
| 397 | 0.00028124  | 0.007651  |
| 398 | 0.00031852  | 0.008739  |
| 399 | 0.000357267 | 0.009989  |
| 400 | 0.000396    | 0.011428  |
| 401 | 0.000433715 | 0.013104  |
| 402 | 0.000473024 | 0.015038  |
| 403 | 0.000517876 | 0.017268  |
| 404 | 0.000572219 | 0.019841  |
| 405 | 0.00064     | 0.022811  |
| 406 | 0.00072456  | 0.02624   |
| 407 | 0.0008255   | 0.0302    |
| 408 | 0.00094116  | 0.034773  |
| 409 | 0.00106988  | 0.040055  |
| 410 | 0.00121     | 0.046155  |
| 411 | 0.001362091 | 0.051431  |
| 412 | 0.001530752 | 0.057325  |
| 413 | 0.001720368 | 0.06391   |
| 414 | 0.001935323 | 0.071264  |
| 415 | 0.00218     | 0.079477  |
| 416 | 0.0024548   | 0.088645  |
| 417 | 0.002764    | 0.098878  |
| 418 | 0.0031178   | 0.110297  |
| 419 | 0.0035264   | 0.123034  |
| 420 | 0.004       | 0.137237  |
| 421 | 0.00454624  | 0.146047  |
| 422 | 0.00515932  | 0.155409  |
| 423 | 0.00582928  | 0.16535   |
| 424 | 0.00654616  | 0.175902  |
| 425 | 0.0073      | 0.187096  |
| 426 | 0.008086507 | 0.198964  |
| 427 | 0.00890872  | 0.21154   |
| 428 | 0.00976768  | 0.224858  |
| 429 | 0.01066443  | 0.238954  |
| 430 | 0.0116      | 0.253865  |
| 431 | 0.01257317  | 0.266176  |
| 432 | 0.01358272  | 0.279     |
| 433 | 0.01462968  | 0.29235   |
| 434 | 0.01571509  | 0.306239  |
| 435 | 0.01684     | 0.320679  |
| 436 | 0.01800736  | 0.335684  |
| 437 | 0.01921448  | 0.351265  |
| 438 | 0.02045392  | 0.367435  |
| 439 | 0.02171824  | 0.384205  |
| 440 | 0.023       | 0.401587  |
| 441 | 0.02429461  | 0.415459  |
| 442 | 0.02561024  | 0.429639  |
| 443 | 0.02695857  | 0.444126  |
| 444 | 0.02835125  | 0.458915  |
| 445 | 0.0298      | 0.474003  |
| 446 | 0.03131083  | 0.489382  |
| 447 | 0.03288368  | 0.505051  |
| 448 | 0.03452112  | 0.520999  |
| 449 | 0.03622571  | 0.537223  |
| 450 | 0.038       | 0.553715  |
| 451 | 0.03984667  | 0.56863   |
| 452 | 0.041768    | 0.583694  |
| 453 | 0.043766    | 0.598893  |
| 454 | 0.04584267  | 0.614217  |
| 455 | 0.048       | 0.629654  |
| 456 | 0.05024368  | 0.645191  |
| 457 | 0.05257304  | 0.660812  |
| 458 | 0.05498056  | 0.676507  |
| 459 | 0.05745872  | 0.692256  |
| 460 | 0.06        | 0.708048  |
| 461 | 0.06260197  | 0.723532  |
| 462 | 0.06527752  | 0.739008  |
| 463 | 0.06804208  | 0.75446   |
| 464 | 0.07091109  | 0.769869  |
| 465 | 0.0739      | 0.785216  |

|     | Photopic    | Melanopic |
| --- | ----------- | --------- |
| 466 | 0.077016    | 0.800481  |
| 467 | 0.0802664   | 0.815643  |
| 468 | 0.0836668   | 0.830679  |
| 469 | 0.0872328   | 0.845571  |
| 470 | 0.09098     | 0.86029   |
| 471 | 0.09491755  | 0.872405  |
| 472 | 0.09904584  | 0.88423   |
| 473 | 0.1033674   | 0.89574   |
| 474 | 0.1078846   | 0.906916  |
| 475 | 0.1126      | 0.917734  |
| 476 | 0.117532    | 0.928169  |
| 477 | 0.1226744   | 0.938197  |
| 478 | 0.1279928   | 0.947794  |
| 479 | 0.1334528   | 0.956938  |
| 480 | 0.13902     | 0.965604  |
| 481 | 0.1446764   | 0.971753  |
| 482 | 0.1504693   | 0.977347  |
| 483 | 0.1564619   | 0.98237   |
| 484 | 0.1627177   | 0.9868    |
| 485 | 0.1693      | 0.990622  |
| 486 | 0.1762431   | 0.993814  |
| 487 | 0.1835581   | 0.996364  |
| 488 | 0.1912735   | 0.998254  |
| 489 | 0.199418    | 0.999471  |
| 490 | 0.20802     | 1         |
| 491 | 0.2171199   | 0.999832  |
| 492 | 0.2267345   | 0.998957  |
| 493 | 0.2368571   | 0.997369  |
| 494 | 0.2474812   | 0.995059  |
| 495 | 0.2586      | 0.992021  |
| 496 | 0.2701849   | 0.988257  |
| 497 | 0.2822939   | 0.983766  |
| 498 | 0.2950505   | 0.978548  |
| 499 | 0.308578    | 0.972608  |
| 500 | 0.323       | 0.965951  |
| 501 | 0.3384021   | 0.958588  |
| 502 | 0.3546858   | 0.950526  |
| 503 | 0.3716986   | 0.941781  |
| 504 | 0.3892875   | 0.932367  |
| 505 | 0.4073      | 0.9223    |
| 506 | 0.4256299   | 0.911597  |
| 507 | 0.4443096   | 0.900281  |
| 508 | 0.4633944   | 0.888376  |
| 509 | 0.4829395   | 0.875903  |
| 510 | 0.503       | 0.862887  |
| 511 | 0.5235693   | 0.848186  |
| 512 | 0.544512    | 0.833038  |
| 513 | 0.56569     | 0.817476  |
| 514 | 0.5869653   | 0.80153   |
| 515 | 0.6082      | 0.785234  |
| 516 | 0.6293456   | 0.768617  |
| 517 | 0.6503068   | 0.751716  |
| 518 | 0.6708752   | 0.734563  |
| 519 | 0.6908424   | 0.71719   |
| 520 | 0.71        | 0.699628  |
| 521 | 0.7281852   | 0.681754  |
| 522 | 0.7454636   | 0.663768  |
| 523 | 0.7619694   | 0.645696  |
| 524 | 0.7778368   | 0.62757   |
| 525 | 0.7932      | 0.609422  |
| 526 | 0.8081104   | 0.59128   |
| 527 | 0.8224962   | 0.573171  |
| 528 | 0.8363068   | 0.555121  |
| 529 | 0.8494916   | 0.537159  |
| 530 | 0.862       | 0.519309  |
| 531 | 0.8738108   | 0.501594  |
| 532 | 0.8849624   | 0.484037  |
| 533 | 0.8954936   | 0.466662  |
| 534 | 0.9054432   | 0.449487  |
| 535 | 0.9148501   | 0.432534  |
| 536 | 0.9237348   | 0.41582   |
| 537 | 0.9320924   | 0.399364  |
| 538 | 0.9399226   | 0.383183  |
| 539 | 0.9472252   | 0.367292  |
| 540 | 0.954       | 0.351707  |
| 541 | 0.9602561   | 0.336519  |
| 542 | 0.9660074   | 0.321656  |

-continued

|  | Photopic | Melanopic |
|---|---|---|
| 543 | 0.9712606 | 0.30713 |
| 544 | 0.9760225 | 0.292953 |
| 545 | 0.9803 | 0.279135 |
| 546 | 0.9840924 | 0.265686 |
| 547 | 0.9874182 | 0.252613 |
| 548 | 0.9903128 | 0.239924 |
| 549 | 0.9928116 | 0.227626 |
| 550 | 0.9949501 | 0.215722 |
| 551 | 0.9967108 | 0.204171 |
| 552 | 0.9980983 | 0.193028 |
| 553 | 0.999112 | 0.182295 |
| 554 | 0.9997482 | 0.171971 |
| 555 | 1 | 0.162056 |
| 556 | 0.9998567 | 0.152549 |
| 557 | 0.9993046 | 0.143447 |
| 558 | 0.9983255 | 0.134745 |
| 559 | 0.9968987 | 0.12644 |
| 560 | 0.995 | 0.118526 |
| 561 | 0.9926005 | 0.110943 |
| 562 | 0.9897426 | 0.103744 |
| 563 | 0.9864444 | 0.096917 |
| 564 | 0.9827241 | 0.090455 |
| 565 | 0.9786 | 0.084346 |
| 566 | 0.9740837 | 0.078579 |
| 567 | 0.9691712 | 0.073143 |
| 568 | 0.9638568 | 0.068026 |
| 569 | 0.9581349 | 0.063217 |
| 570 | 0.952 | 0.058701 |
| 571 | 0.9454504 | 0.054443 |
| 572 | 0.9384992 | 0.050457 |
| 573 | 0.9311628 | 0.046732 |
| 574 | 0.9234576 | 0.043253 |
| 575 | 0.9154 | 0.040009 |
| 576 | 0.9070064 | 0.036986 |
| 577 | 0.8982772 | 0.034174 |
| 578 | 0.8892048 | 0.031558 |
| 579 | 0.8797816 | 0.029129 |
| 580 | 0.87 | 0.026875 |
| 581 | 0.8598613 | 0.024784 |
| 582 | 0.849392 | 0.022848 |
| 583 | 0.838622 | 0.021055 |
| 584 | 0.8275813 | 0.019396 |
| 585 | 0.8163 | 0.017862 |
| 586 | 0.8047947 | 0.016446 |
| 587 | 0.793082 | 0.015137 |
| 588 | 0.781192 | 0.01393 |
| 589 | 0.7691547 | 0.012817 |
| 590 | 0.757 | 0.01179 |
| 591 | 0.7447541 | 0.010839 |
| 592 | 0.7324224 | 0.009964 |
| 593 | 0.7200036 | 0.009158 |
| 594 | 0.7074965 | 0.008416 |
| 595 | 0.6949 | 0.007734 |
| 596 | 0.6822192 | 0.007107 |
| 597 | 0.6694716 | 0.006531 |
| 598 | 0.6566744 | 0.006001 |
| 599 | 0.6438448 | 0.005514 |
| 600 | 0.631 | 0.005067 |
| 601 | 0.6181555 | 0.004655 |
| 602 | 0.6053144 | 0.004277 |
| 603 | 0.5924756 | 0.003929 |
| 604 | 0.5796379 | 0.00361 |
| 605 | 0.5668 | 0.003318 |
| 606 | 0.5539611 | 0.003049 |
| 607 | 0.5411372 | 0.002802 |
| 608 | 0.5283528 | 0.002576 |
| 609 | 0.5156323 | 0.002368 |
| 610 | 0.503 | 0.002177 |
| 611 | 0.4904688 | 0.002002 |
| 612 | 0.4780304 | 0.001841 |
| 613 | 0.4656776 | 0.001693 |
| 614 | 0.4534032 | 0.001558 |
| 615 | 0.4412 | 0.001433 |
| 616 | 0.42908 | 0.001319 |
| 617 | 0.417036 | 0.001214 |
| 618 | 0.405032 | 0.001117 |
| 619 | 0.393032 | 0.001029 |

-continued

|  | Photopic | Melanopic |
|---|---|---|
| 620 | 0.381 | 0.000947 |
| 621 | 0.3689184 | 0.000872 |
| 622 | 0.3568272 | 0.000803 |
| 623 | 0.3447768 | 0.00074 |
| 624 | 0.3328176 | 0.000681 |
| 625 | 0.321 | 0.000628 |
| 626 | 0.3093381 | 0.000578 |
| 627 | 0.2978504 | 0.000533 |
| 628 | 0.2865936 | 0.000491 |
| 629 | 0.2756245 | 0.000453 |
| 630 | 0.265 | 0.000418 |
| 631 | 0.2547632 | 0.000386 |
| 632 | 0.2448896 | 0.000356 |
| 633 | 0.2353344 | 0.000328 |
| 634 | 0.2260528 | 0.000303 |
| 635 | 0.217 | 0.00028 |
| 636 | 0.2081616 | 0.000258 |
| 637 | 0.1995488 | 0.000239 |
| 638 | 0.1911552 | 0.000221 |
| 639 | 0.1829744 | 0.000204 |
| 640 | 0.175 | 0.000188 |
| 641 | 0.1672235 | 0.000174 |
| 642 | 0.1596464 | 0.000161 |
| 643 | 0.1522776 | 0.000149 |
| 644 | 0.1451259 | 0.000138 |
| 645 | 0.1382 | 0.000127 |
| 646 | 0.1315003 | 0.000118 |
| 647 | 0.1250248 | 0.000109 |
| 648 | 0.1187792 | 0.000101 |
| 649 | 0.1127691 | 0.000093 |
| 650 | 0.107 | 0.000087 |
| 651 | 0.1014762 | 0.00008 |
| 652 | 0.09618864 | 0.000074 |
| 653 | 0.09112296 | 0.000069 |
| 654 | 0.08626485 | 0.000064 |
| 655 | 0.0816 | 0.000059 |
| 656 | 0.07712064 | 0.000055 |
| 657 | 0.07282552 | 0.000051 |
| 658 | 0.06871008 | 0.000047 |
| 659 | 0.06476976 | 0.000044 |
| 660 | 0.061 | 0.000041 |
| 661 | 0.05739621 | 0.000038 |
| 662 | 0.05395504 | 0.000035 |
| 663 | 0.05067376 | 0.000033 |
| 664 | 0.04754965 | 0.00003 |
| 665 | 0.04458 | 0.000028 |
| 666 | 0.04175872 | 0.000026 |
| 667 | 0.03908496 | 0.000024 |
| 668 | 0.03656384 | 0.000023 |
| 669 | 0.03420048 | 0.000021 |
| 670 | 0.032 | 0.00002 |
| 671 | 0.02996261 | 0.000018 |
| 672 | 0.02807664 | 0.000017 |
| 673 | 0.02632936 | 0.000016 |
| 674 | 0.02470805 | 0.000015 |
| 675 | 0.0232 | 0.000014 |
| 676 | 0.02180077 | 0.000013 |
| 677 | 0.02050112 | 0.000012 |
| 678 | 0.01928108 | 0.000011 |
| 679 | 0.01812069 | 0.00001 |
| 680 | 0.017 | 0.00001 |
| 681 | 0.01590379 | 0.000009 |
| 682 | 0.01483718 | 0.000008 |
| 683 | 0.01381068 | 0.000008 |
| 684 | 0.01283478 | 0.000007 |
| 685 | 0.01192 | 0.000007 |
| 686 | 0.01106831 | 0.000006 |
| 687 | 0.01027339 | 0.000006 |
| 688 | 0.009533311 | 0.000005 |
| 689 | 0.008846157 | 0.000005 |
| 690 | 0.00821 | 0.000005 |
| 691 | 0.007623781 | 0.000004 |
| 692 | 0.007085424 | 0.000004 |
| 693 | 0.006591476 | 0.000004 |
| 694 | 0.006138485 | 0.000004 |
| 695 | 0.005723 | 0.000003 |
| 696 | 0.005343059 | 0.000003 |

|  | Photopic | Melanopic |
|---|---|---|
| 697 | 0.004995796 | 0.000003 |
| 698 | 0.004676404 | 0.000003 |
| 699 | 0.004380075 | 0.000003 |
| 700 | 0.004102 | 0.000002 |
| 701 | 0.003838453 | 0.000002 |
| 702 | 0.003589099 | 0.000002 |
| 703 | 0.003354219 | 0.000002 |
| 704 | 0.003134093 | 0.000002 |
| 705 | 0.002929 | 0.000002 |
| 706 | 0.002738139 | 0.000002 |
| 707 | 0.002559876 | 0.000002 |
| 708 | 0.002393244 | 0.000001 |
| 709 | 0.002237275 | 0.000001 |
| 710 | 0.002091 | 0.000001 |
| 711 | 0.001953587 | 0.000001 |
| 712 | 0.00182458 | 0.000001 |
| 713 | 0.00170358 | 0.000001 |
| 714 | 0.001590187 | 0.000001 |
| 715 | 0.001484 | 0.000001 |
| 716 | 0.001384496 | 0.000001 |
| 717 | 0.001291268 | 0.000001 |
| 718 | 0.001204092 | 0.000001 |
| 719 | 0.001122744 | 0.000001 |
| 720 | 0.001047 | 0.000001 |
| 721 | 0.00097659 | 0.000001 |
| 722 | 0.000911109 | 0.000001 |
| 723 | 0.000850133 | 0.000001 |
| 724 | 0.000793238 | 0.000001 |
| 725 | 0.00074 | 0 |
| 726 | 0.000690083 | 0 |
| 727 | 0.00064331 | 0 |
| 728 | 0.000599496 | 0 |
| 729 | 0.000558455 | 0 |
| 730 | 0.00052 | 0 |
| 731 | 0.000483914 | 0 |
| 732 | 0.000450053 | 0 |
| 733 | 0.000418345 | 0 |
| 734 | 0.000388718 | 0 |
| 735 | 0.0003611 | 0 |
| 736 | 0.000335384 | 0 |
| 737 | 0.00031144 | 0 |
| 738 | 0.000289166 | 0 |
| 739 | 0.000268454 | 0 |
| 740 | 0.0002492 | 0 |
| 741 | 0.000231302 | 0 |
| 742 | 0.000214686 | 0 |
| 743 | 0.000199288 | 0 |
| 744 | 0.000185048 | 0 |
| 745 | 0.0001719 | 0 |
| 746 | 0.000159778 | 0 |
| 747 | 0.000148604 | 0 |
| 748 | 0.000138302 | 0 |
| 749 | 0.000128793 | 0 |
| 750 | 0.00012 | 0 |
| 751 | 0.00011186 | 0 |
| 752 | 0.000104322 | 0 |
| 753 | 9.73356E-05 | 0 |
| 754 | 9.08459E-05 | 0 |
| 755 | 0.0000848 | 0 |
| 756 | 7.91467E-05 | 0 |
| 757 | 0.000073858 | 0 |
| 758 | 0.000068916 | 0 |
| 759 | 6.43027E-05 | 0 |
| 760 | 0.00006 | 0 |
| 761 | 5.59819E-05 | 0 |
| 762 | 5.22256E-05 | 0 |
| 763 | 4.87184E-05 | 0 |
| 764 | 4.54475E-05 | 0 |
| 765 | 0.0000424 | 0 |
| 766 | 3.9561E-05 | 0 |
| 767 | 3.69151E-05 | 0 |
| 768 | 3.44487E-05 | 0 |
| 769 | 3.21482E-05 | 0 |
| 770 | 0.00003 | 0 |
| 771 | 2.79913E-05 | 0 |
| 772 | 2.61136E-05 | 0 |
| 773 | 2.43602E-05 | 0 |
| 774 | 2.27246E-05 | 0 |
| 775 | 0.0000212 | 0 |
| 776 | 1.97789E-05 | 0 |
| 777 | 1.84529E-05 | 0 |
| 778 | 1.72169E-05 | 0 |
| 779 | 1.60646E-05 | 0 |
| 780 | 0.00001499 | 0 |

Figure 7:
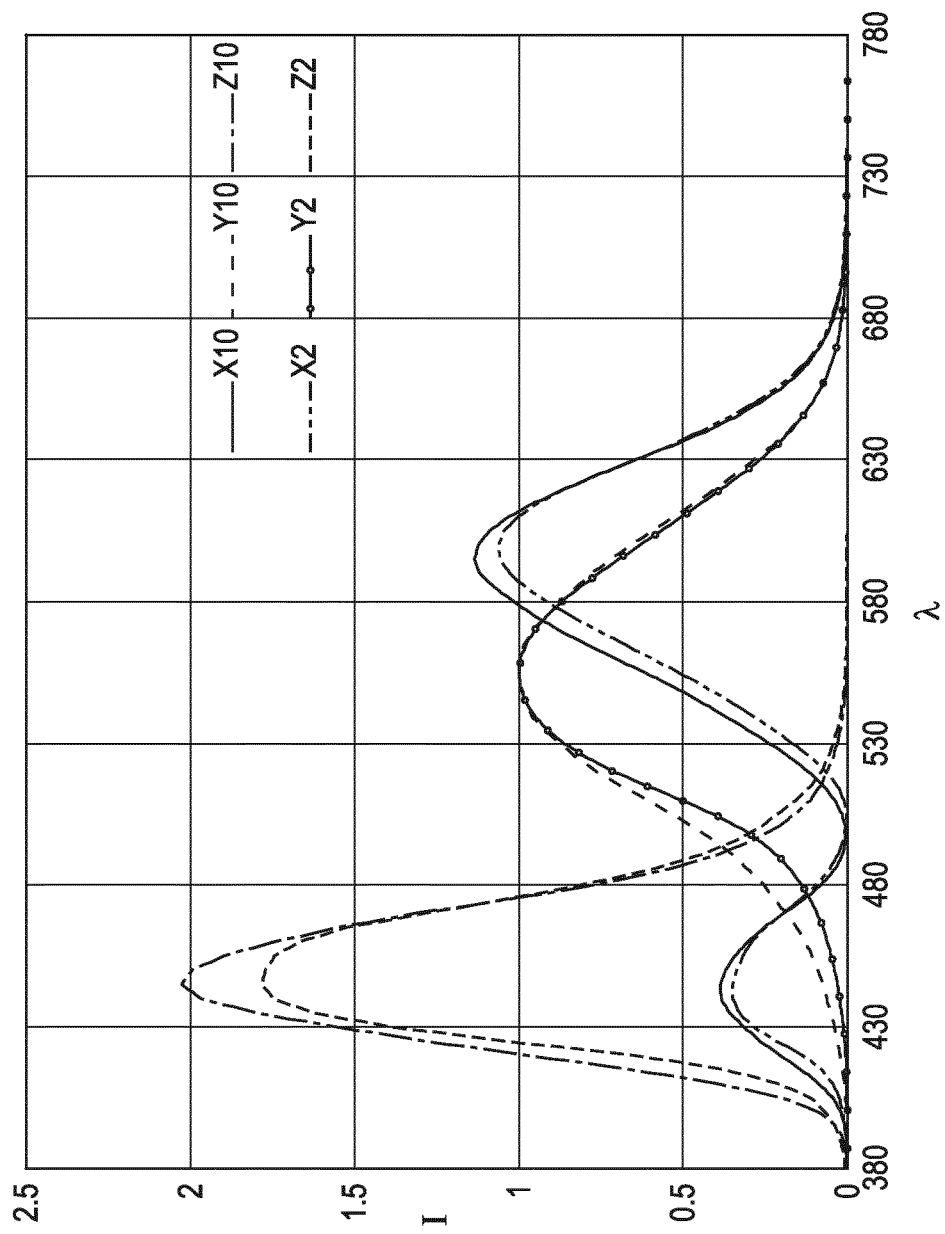
FIG. 7 provides the 2° and 10° color matching functions (such as derived from CIE S 014-1/E:2006).

FIG. 7 provides the 2° and 10° color matching functions (such as derived from CIE S 014-1/E:2006).

The term "plurality" refers to two or more.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%.

The term "comprise" includes also embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A light generating system configured to generate system light, wherein the light generating system comprises a first light generating device and a second light generating device, wherein:
the first light generating device is configured to generate first device light, wherein the first light generating device comprises (i) a first light source configured to generate first light source light having a first dominant wavelength $\lambda d1$ selected from the range of 470-500 nm, and (ii) a first luminescent material configured to convert part of the first light source light into first luminescent material light; wherein the first device light comprises the first light source light and the first luminescent material light;
and wherein the first device light has a first color point;
the second light generating device is configured to generate second device light, wherein the second light generating device comprises (i) a second light source configured to generate second light source light having a second dominant wavelength $\lambda d2$, and (ii) a second luminescent material configured to convert at least part of the second light source light into second luminescent material light; wherein the second device light comprises the second luminescent material light and optionally the second light source light; and wherein the second device light is white light having a second color point and a second correlated color temperature Tc2;
$\lambda d1\lambda 2 \geq 10$ nm;
spectral power distributions of the first light source light and the second light source light differ; and
the first color point and the second color point differ by a maximum of 0.03 for u' and/or by a maximum of 0.03 for v', with the color points based on 10° Color matching functions, the light generating system further comprising a third light generating device, wherein:
the third light generating device is configured to generate third device light, wherein the third light generating device comprises (i) a third light source configured to generate third light source light having a third dominant wavelength $\lambda d3$, and (ii) a third luminescent material configured to convert at least part of the third light source light into third luminescent material light; wherein the third device light comprises the third luminescent material light and optionally the third light source light; and wherein the third device light is white light having a third color point and a third correlated color temperature Tc3;
$\lambda d1\lambda 3 \geq 10$ nm;
spectral power distributions of the first light source light and the third light source light differ; and
the system light comprises one or more of the first device light, the second device light, and third device light; and
Tc2-Tc3$\geq$700 K, and the light generating system further comprising (i) a first string comprising one or more first light generating devices and one or more second light generating devices and (ii) a second string comprising one or more third light generating devices, wherein the light sources comprise solid state light sources.

2. The light generating system according claim 1, wherein the first luminescent material is configured to convert part of the first light source light into first luminescent material light having a first luminescent material dominant wavelength $\lambda dL1$ selected from the range of 575-638 nm, and wherein the second correlated color temperature Tc2 of the second device light is at least 3400 K.

3. The light generating system according to claim 1, wherein the first dominant wavelength $\lambda d1$ is selected from the range of 478-484 nm, and wherein the first luminescent material is configured to convert part of the first light source light into first luminescent material light having a first luminescent material dominant wavelength $\lambda dL1$ selected from the range of 575-612 nm.

4. The light generating system according to claim 1, comprising a first LED string comprising one or more first light generating devices and one or more second light generating devices, having a ratio of (a) number n1 of first light generating devices and (b) a number n2 of second light generating devices, with of $0.05 \leq n1/n2 \leq 20$, and wherein the light sources comprise solid state light sources.

5. The light generating system according to any one of the claim 4, further comprising an input device selected from the group consisting of a user interface, a time device, and a sensor, wherein the control system is configured to control a spectral power distribution of the system light in response to a signal of the input device.

6. The light generating system according to claim 5, wherein the control system is configured to control the spectral power distribution of the system light of the light generating system.

7. The light generating system according to any one of the claim 1, wherein the second dominant wavelength $\lambda d2$ is selected from the range of 430-470 nm.

8. The light generating system according to claim 7, wherein the third luminescent material comprises a narrow band red emitting phosphor based on $Mn_{4+}$.

9. The light generating system according to claims 8, wherein the control system is configured to control in an operational mode the spectral power distribution of the system light while maintaining a predefined MDER value.

10. The light generating system according to any one of the claim 7, further comprising a control system configured to control one or more of the first light generating device, the second light generating device, and the third light generating device.

11. The light generating system according to claim 10, wherein the control system is configured to individually control (a) a set comprising the first light generating device and the second light generating device, and (b) the third light generating device.

12. The light generating system according to claim 7, wherein Tc2-Tc3≥1000 K.

13. The light generating system according to claim 1, wherein the second luminescent material and the third luminescent material comprise phosphors configured to provide luminescent material light having a full width half maximum of at least 40 nm, wherein Tc2-Tc3≥2500 K, and wherein the first color point and the second color point differ at maximum 0.01 for u' and/or at maximum 0.01 for v'.

14. The light generating system according to claim 1, wherein in an operational mode of the light generation system the system light has a CRI of at least 80, an R9 value of at least 50, and an MDER value selected from the range of at least 0.45, wherein MDER is defined as:

$$MDER = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3a)}$$

wherein $SPD(\lambda)$ is the spectral power distribution of the system light, $m(\lambda)$ is the melanopic sensitivity function, the $V(\lambda)$ is the photopic luminosity function.

15. A lamp or a luminaire comprising the light generating system according to claim 1.

\* \* \* \* \*